(12) United States Patent
Jiang et al.

(10) Patent No.: US 11,752,212 B2
(45) Date of Patent: Sep. 12, 2023

(54) N-OXIDE AND ECTOINE MONOMERS, POLYMERS, THEIR COMPOSITIONS, AND RELATED METHODS

(71) Applicant: University of Washington, Seattle, WA (US)

(72) Inventors: Shaoyi Jiang, Redmond, WA (US); Priyesh Jain, Seattle, WA (US); Jinrong Ma, Seattle, WA (US); Bowen Li, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 397 days.

(21) Appl. No.: 16/627,068

(22) PCT Filed: Jun. 29, 2018

(86) PCT No.: PCT/US2018/040448
§ 371 (c)(1),
(2) Date: Dec. 27, 2019

(87) PCT Pub. No.: WO2019/006398
PCT Pub. Date: Jan. 3, 2019

(65) Prior Publication Data
US 2020/0123294 A1 Apr. 23, 2020

Related U.S. Application Data

(60) Provisional application No. 62/526,591, filed on Jun. 29, 2017.

(51) Int. Cl.
| | | |
|---|---|---|
| A61K 47/58 | (2017.01) | |
| A61K 9/51 | (2006.01) | |
| A61L 27/34 | (2006.01) | |
| A61L 29/08 | (2006.01) | |
| A61L 31/10 | (2006.01) | |
| C08F 220/60 | (2006.01) | |
| C08J 3/075 | (2006.01) | |
| C09D 5/16 | (2006.01) | |
| C12N 5/078 | (2010.01) | |
| C08F 222/22 | (2006.01) | |

(52) U.S. Cl.
CPC ........... *A61K 47/58* (2017.08); *A61K 9/5138* (2013.01); *A61L 27/34* (2013.01); *A61L 29/085* (2013.01); *A61L 31/10* (2013.01); *C08F 220/60* (2013.01); *C08J 3/075* (2013.01); *C09D 5/16* (2013.01); *C12N 5/0644* (2013.01); *C08F 220/603* (2020.02); *C08F 222/225* (2020.02); *C08J 2300/206* (2013.01); *C08J 2333/26* (2013.01)

(58) Field of Classification Search
CPC ...... A61K 47/58; C08F 220/603; C08F 20/60
See application file for complete search history.

(56) References Cited

U.S. PATENT DOCUMENTS

| | | | | |
|---|---|---|---|---|
| 5,877,209 | A * | 3/1999 | Yunis | A61K 8/347 514/458 |
| 6,375,932 | B1 * | 4/2002 | Hiwatashi | A61Q 5/06 424/70.13 |
| 6,696,089 | B2 | 2/2004 | Kabanov et al. | |
| 8,268,296 | B2 | 9/2012 | Knappe et al. | |
| 2005/0025805 | A1 * | 2/2005 | Heller | A61P 29/00 424/617 |
| 2006/0217285 | A1 * | 9/2006 | Destarac | A61K 8/90 510/475 |
| 2015/0217030 | A1 * | 8/2015 | Benkoski | A61L 31/16 424/443 |

FOREIGN PATENT DOCUMENTS

| | | | |
|---|---|---|---|
| EP | 3 384 917 A1 | 10/2018 | |
| GB | 2 041 944 A | 9/1980 | |
| JP | 2001-310915 A | 11/2001 | |
| WO | 2000/002937 A1 | 1/2000 | |
| WO | WO-2016108041 A1 * | 7/2016 | ............ A01N 37/36 |
| WO | 2017/041834 A1 | 3/2017 | |
| WO | 2017/095264 A1 | 6/2017 | |

OTHER PUBLICATIONS

Wikipedia:Hair, 1 page.*
Parzuchowski et al., JACS, 2002, 124, 12182-12191.*
Chemspider, N,N-dimethylaminopropyl acrylamide, 1 page.*
Kim et al. Nature, 441/18, 2006, 362-365 (Year: 2006).*
Kenney Polymer Engineering and Science, 8/3, 1968, 216-226 (Year: 1968).*
Ma, Study of a Novel Zwitterionic Material and Its Biological Applications. Diss. 2018, 43 pages.*
Supplementary European Search Report dated Feb. 24, 2021, issued in corresponding European Application 18824413.1 filed Jun. 29, 2018, 21 pages.
International Search Report and Written Opinion dated Jan. 17, 2019, issued in corresponding International Application No. PCT/US2018/40448, filed Jun. 29, 2018, 11 pages.
Smeets, N.M.B., and T. Hoare, "Designing Responsive Microgels for Drug Delivery Applications," Journal of Polymer Science Part A: Polymer Chemistry 51(14)13027-3043, Apr. 2013.
Office Action dated Aug. 1, 2022, issued in corresponding Japanese Patent Application No. 2019-572481, filed Jun. 29, 2018, 8 pages.
Office Action dated Jan. 18, 2023, issued in corresponding Chinese Application No. 201880055355.7, filed Jun. 29, 2018, 14 pages.
Notice of Reasons for Rejection dated Feb. 20, 2023, issued in corresponding Japanese Application No. 2019-572481, filed Jun. 29, 2018, 7 pages.

* cited by examiner

*Primary Examiner* — Kyle A Purdy
(74) *Attorney, Agent, or Firm* — Christensen O'Connor Johnson Kindness PLLC

(57) ABSTRACT

N-oxide and monomers, N-oxide polymers and copolymers, methods for making the N-oxide monomers, polymers, and copolymers, compositions and materials that include N-oxide polymers and copolymers, and methods for using the N-oxide monomers, N-oxide polymers, and N-oxide copolymers.

12 Claims, 10 Drawing Sheets

| Sample | %Discs | %Spheres | %Dendrites | Score Day 5 | Score Day 7 |
|---|---|---|---|---|---|
| Control | 65, 55 | 30, 25 | 1, 5 | 321 | 275 |
| N-oxide gel (600 Pa) | 80, 70 | 20, 25 | 0, 5 | 360 | 335 |
| Fresh | 90, 90 | 10, 10 | 0, 0 | 380 | 380 |

*Fig. 3* ic acid) is a pyrimidine derivative where all except one double bond have been hydrogenated. Most important characteristic of this molecule is the delocalized it-bonding in the N—C—N group which results in a permanent zwitterionic structure.

N-OXIDE AND ECTOINE MONOMERS, POLYMERS, THEIR COMPOSITIONS, AND RELATED METHODS

CROSS-REFERENCE TO RELATED APPLICATION

This application claims the benefit of Application No. 62/526,591, filed Jun. 29, 2018, incorporated herein by reference in its entirety.

STATEMENT OF GOVERNMENT LICENSE RIGHTS

This invention was made with Government support under N00014-16-1-3084 awarded by the Office of Naval Research (ONR), HDTRA1-13-1-0044 awarded by the Defense Threat Reduction Agency (DTRA), and DMR1708436 awarded by the National Science Foundation (NSF). The Government has certain rights in the invention.

BACKGROUND OF THE INVENTION

Trimethylamine oxide (TMAO) is the most potent among all protecting osmolytes and has been shown to strongly bolster protein stability to counteract severe denaturing stress in a variety of organisms. Sharks, skates, and rays are known to accumulate TMAO in order to counteract urea denaturation. The protein folding ability of TMAO has been utilized to study the mechanisms associated with protein misfolding diseases, such as Alzheimer's and prion diseases, as well as neuroblastoma and glaucoma.

Several halophilic organism accumulates protecting osmolyte called ectoine to protect their biopolymers against high temperature and salty environmental conditions. Ectoines are receiving increasing attention by the scientific community because of its numerous applications as protecting agents for macromolecules, cells and tissues, together with their potential as therapeutic agents for certain diseases. Compared to other compatible solutes, ectoine possess additional protective properties that stabilizes even whole cells against UV radiation or cytotoxins and also protects skin from the effects of UVA-induced cell damage. These protective properties makes ectoine a valuable compound in health care and skin care industries. Structurally, ectoine (1,4,5,6-tetrahydro-2-methyl-4-pyrimidine carboxylic acid) is a pyrimidine derivative where all except one double bond have been hydrogenated. Most important characteristic of this molecule is the delocalized it-bonding in the N—C—N group which results in a permanent zwitterionic structure.

A need exists to develop improved nonfouling polymers and compositions and materials that include these polymers having advantageous nonfouling properties. The present invention seeks to fulfill this need and provides further related advantages.

SUMMARY OF THE INVENTION

In one aspect, the present invention provides N-oxide monomers, N-oxide polymers and copolymers, methods for making the N-oxide monomers, polymers, and copolymers, compositions and materials that include N-oxide polymers and copolymers, and methods for using the N-oxide monomers, N-oxide polymers, and N-oxide copolymers.

In another aspect, the present invention provides ectoine monomers, ectoine polymers and copolymers, methods for making the ectoine monomers, polymers, and copolymers, compositions and materials that include ectoine polymers and copolymers, and methods for using the ectoine monomers, ectoine polymers, and ectoine copolymers.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 3 tabulates platelet preservation using a representative N-oxide polymer hydrogel versus Control (blood bag without N-oxide polymer hydrogel). The first and second entries under % Discs, % Sphere, and % Dendrites refer to platelet preservation after days 5 and 7, respectively.

DETAILED DESCRIPTION OF THE INVENTION

Figure 1:
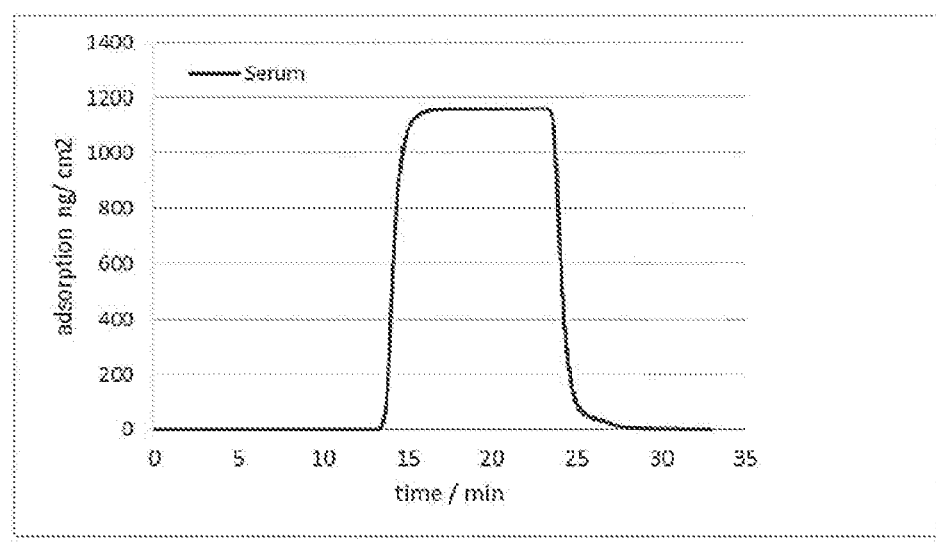
FIG. 1 shows surface plasmon resonance (SPR) data of a representative N-oxide polymer surface, DMAPA N-oxide brushes, prepared by grafting from a gold substrate via ATRP. The N-oxide polymer surface has a film thickness of 10 nm and exhibited 2.2 ng/cm$^2$ adsorbed protein.

In one aspect, the present invention provides N-oxide monomers, N-oxide polymers and copolymers, methods for making the N-oxide monomers, polymers, and copolymers, compositions and materials that include N-oxide polymers and copolymers, and methods for using the N-oxide monomers, N-oxide polymers, and N-oxide copolymers.

In another aspect, the present invention provides ectoine monomers, ectoine polymers and copolymers, methods for making the ectoine monomers, polymers, and copolymers, compositions and materials that include ectoine polymers and copolymers, and methods for using the ectoine monomers, ectoine polymers, and ectoine copolymers.

N-Oxide Monomers, Polymers, Copolymers and their Uses

The present invention provides N-oxide monomers, N-oxide polymers and copolymers, methods for making the N-oxide monomers, polymers, and copolymers, compositions and materials that include N-oxide polymers and copolymers, and methods for using the N-oxide polymers and N-oxide copolymers.

As described herein, the N-oxide monomers can be readily polymerized under standard polymerizing conditions to provide polymers of the solutes. The polymers can be linear, branched, star or crosslinked, which are able to further withstand nonspecific biofouling and provide strong hydration in different manners.

N-Oxide Monomers, Polymers, and Copolymers

In certain aspects, the present invention provides N-oxide monomers and polymers and copolymers prepared from N-oxide monomers.

Monomers of the invention include (a) N-oxide monomers with backbones selected from silicone, fluorinated, peptide, urethane, urea, and imide backbones, and degradable backbones beyond methacrylate and acrylate backbones, (b) linear N-oxide crosslinkers, degradable and non-degradable N-oxide based crosslinkers, (c) linear N-oxide based monomers that provide N-oxide groups in the polymer backbone or N-oxide groups in the polymer side chains, or (d) N-oxide monomers with conducting backbones.

Polymers and copolymers of the invention include polymers and copolymers, such as homopolymers, random copolymers, block copolymers, multiblock copolymers, and branched or star polymers that include repeating units containing N-oxide groups, including such polymers prepared from polymerization (or copolymerization) of one or more monomers of the invention (e.g., N-oxide containing monomers).

The polymers and copolymers can be advantageously used in a variety of applications, such as medical device/cell therapeutics, biopharma and chemical/marine applications, cosmetic products (e.g., as an additive in moisturizers, facial/body creams, cosmetic makeups, face masks and shampoo/conditioners to retain water or moisture), and in energy devices (e.g., increase energy efficacy due to dipole).

N-oxide monomers.

In one aspect, the invention provides N-oxide monomers. The N-oxide monomers provide N-oxide group-containing polymers and copolymers that include N-oxide group-containing repeating units. The N-oxide groups of the repeating units and polymers may be pendant N-oxide groups (i.e., polymer side chains) or N-oxide groups that are part of the polymer backbone.

In certain embodiments, N-oxide monomers include monomers that provide polymers or copolymers having pendant N-oxide groups (polymer side chains). Representative N-oxide monomers have formula (I):

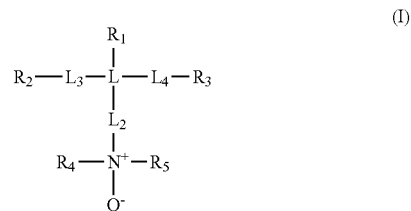

wherein $R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from functional groups suitable for polymerization by addition, condensation or free radical polymerization;

$R_4$ and $R_5$ are independently selected from the group consisting of hydrogen, $C_1$-$C_{20}$ alkyl, and $C_6$-$C_{12}$ aryl, cyclic alkyl;

L is C or Si;

$L_2$ is independently selected from —$(CH_2)_x$— or —(CH(CN))$_x$—, where x is an integer from 1 to 20; and $L_3$ and $L_4$ are independently selected from —$(CH_2)_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, preferably from 1 to 20. In certain embodiments, $L_3$ and/or $L_4$ is absent.

Representative monomers include the following compounds:

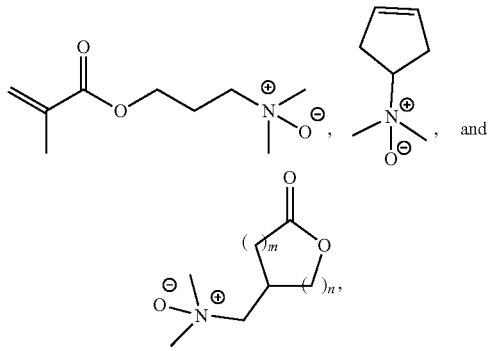

where m and n are independently an integer from 1 to 3.

The preparation of a representative N-oxide monomer useful for making the polymers and copolymers of the invention is described in Example 1.

In certain embodiments, the novel monomers of the invention do not include a monomer having the following structure:

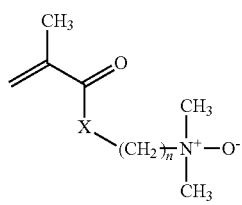

wherein X is O or N, and n=1-10.

It will be appreciated that the N-oxide polymers and copolymers of the invention used for making the inventive surface coatings, bulk materials, standalone materials, hydrogels, and conjugates can be prepared from the monomers described herein, including the methacrylate/methacrylamide N-oxide monomer shown immediately above.

In other embodiments, N-oxide monomers include monomers that provide polymers or copolymers having N-oxide groups in the polymer backbone. Representative N-oxide monomers have formula (II):

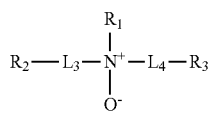

(II)

wherein $R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from functional groups suitable for polymerization by addition, condensation or free radical polymerization; and $L_3$ and $L_4$ are independently selected from —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 0 to 20, preferably from 1 to 20.

N-Oxide Polymers and Copolymers.

In other aspects, the invention provides N-oxide polymers prepared from N-oxide monomers, such as described herein, and that include N-oxide repeating units.

In certain embodiments for these polymers and copolymers, the polymer and copolymer backbone can be any one of a polyester, a polypeptide, a polyimide, a polyphosphazene, a polysiloxane, a polyepoxy, a vinyl polymer, a phenolic polymer, a polyurethane, a polyurea, a polycarbonate, a polysulfone, or a polysulfide.

The N-oxide polymers and copolymers of the invention include polymers and copolymers prepared from monomers of formulae (I) and (II). Polymers can be formed by polymerization of (a) a monomer of formula (I) or (b) a monomer of formula (II). Copolymers can be prepared by copolymerization of (a) a monomer of formula (I) and a second comonomer that is suitable for copolymerization with a monomer of formula (I), (b) a monomer of formula (II) and a second comonomer that is suitable for copolymerization with a monomer of formula (II), and (c) a monomer of formula (I) and a monomer of formula (II) that is suitable for copolymerization with a monomer of formula (I).

In certain embodiments, the N-oxide monomer provides a polymer repeating unit that includes an N-oxide moiety that is pendant from the polymer backbone (i.e., forms a part of the polymer side chain). Representative polymers having N-oxide moieties that are pendant from the polymer backbone have formula (III):

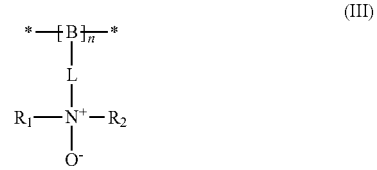

(III)

wherein

* indicates the point of attachment of the repeating unit to other repeating units in the polymer or copolymer;

B is a polymer backbone as described above;

L is a linker group that links the N-oxide moiety to the backbone, representative groups include —(CH$_2$)$_x$—, —(CH(CN))$_x$—, —C(=O)NH(CH$_2$)$_x$—, —C(=O)O(CH$_2$)$_x$—, —C(=O)OC(=O)O(CH$_2$)$_x$—, —(CH$_2$)$_x$—O—(CH$_2$)$_x$—, and —(CH$_2$)$_x$—S—S—(CH$_2$)$_x$—, where x at each occurrence is an integer independently selected from 1 to 20;

$R_1$ and $R_2$ are independently selected from the group consisting of hydrogen, $C_1$-$C_{20}$ alkyl (including cyclic alkyl, e.g., C3-C7 cycloalkyl), and $C_6$-$C_{12}$ aryl; and n is an integer from about 10 to about 500.

In other embodiments, representative polymers having N-oxide moieties that are pendant from the polymer backbone have formula (IV):

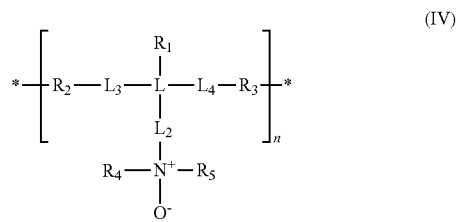

(IV)

wherein $R_1$, $R_2$, $R_3$, $R_4$, $R_5$, L, $L_2$, $L_3$, and $L_4$ are as described above for the monomer of formula (I), with the understanding that $R_2$ and $R_3$ in formula (IV) are the residues of polymerization of the functional groups $R_2$ and $R_3$, respectively, in formula (I); and n is an integer from about 10 to about 500.

In other embodiments, the N-oxide monomer provides a polymer repeating unit that includes an N-oxide moiety that is in the polymer backbone (i.e., forms a part of the polymer backbone). Representative polymers having N-oxide moieties that in the polymer backbone have formula (V):

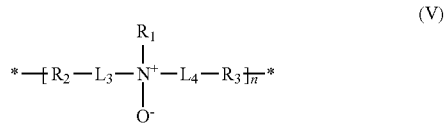

(V)

wherein $R_1$, $R_2$, $R_3$, $L_3$, and $L_4$ are as described above for the monomer of formula (II), with the understanding that $R_2$ and $R_3$ in formula (V) are the residues of polymerization of the functional groups $R_2$ and $R_3$, respectively, in formula (II); and n is an integer from about 10 to about 500.

Conducting N-Oxide Polymers and Copolymers.

In further aspects, the invention provides conducting N-oxide polymers include N-oxide repeating units.

In certain embodiments, the invention provides conducting N-oxide polymer comprising N-oxide moieties in the polymer side chain. Representative conducting polymers have the formula (VI):

$$*-[Ar-(X)_a]_n-*$$
$$|$$
$$(R_1)_b$$
$$|$$
$$R_2-N^+-R_3$$
$$|$$
$$O^-$$

(VI)

wherein

* is the point of attachment of one repeating unit and the next,

—[Ar—(X)$_a$]$_n$— is the polymer backbone,

Ar is selected from arylene, substituted arylene, heteroarylene, substituted heteroarylene, alkylene, substituted alkylene, and alkynylene, X is selected from S, O, N, NH, CH=CH, and C6-C12 arylene, a is 0 or 1, b is 0 or 1, n is an integer from 5 to about 10,000, $R_1$ is C1-C6 substituted or unsubstituted alkylene, $R_2$ and $R_3$ are independently selected from the group consisting of hydrogen, C1-C6 alkyl, substituted C1-C6 alkyl, C6-C12 aryl, and substituted C6-C12 aryl.

In certain embodiments, the invention provides a modified surface that comprises a polymer of formula (VI). The modified surface can be the surface of artificial neural system, neuron-regeneration platform, neural sensor, cell-culture platform; non-fouling semi-conductor, battery, organic solar cell, biofuel cell, printed electronic circuit, organic light-emitting diode, actuator, electrochromism device, supercapacitor, chemical sensor, flexible transparent display, electromagnetic shield, antistatic coating, microwave-absorbent device, or radar-absorptive device.

In certain embodiments, the invention provides a bulk construct that comprises a polymer of formula (VI). Representative constructs can be a medical, electronic, or marine device. In certain of these embodiments, the bulk construct is an artificial neural system, neuron-regeneration platform, neural sensor, cell-culture platform; non-fouling semi-conductor, battery, organic solar cell, biofuel cell, printed electronic circuit, organic light-emitting diode, actuator, electrochromism device, supercapacitor, chemical sensor, flexible transparent display, electromagnetic shield, antistatic coating, microwave-absorbent device, or radar-absorptive device.

Conducting N-oxide polymers can be prepared by depositing a functionalized conducting polymer coating on a surface. The preparation method includes (a) dissolving a monomer that is a precursor of the conducting N-oxide polymer in an aqueous medium to form a monomer solution;

(b) contacting the monomer solution with a surface; and (c) polymerizing the monomers to form a functionalized conducting polymer coating on the surface.

N-Oxide Star Polymers and Copolymers.

In others aspects, the invention provides N-oxide star polymers and copolymers that include N-oxide repeating units.

These polymers include a core and a plurality of N-oxide branches covalently coupled to the core. The cores of these polymers can be a small molecule, an oligomer, or a polymer having a star shape. In certain embodiments, these polymers can include three, four, five, or more N-oxide branches. In certain of these embodiments, one or more of the N-oxide branches may themselves be further branched. In certain embodiments, these polymers can further include terminal functional groups bound to the terminal end of the plurality of N-oxide branches. Representative terminal functional groups are selected from OH, NH, $NH_2$, SH, $N_3$, CH=$CH_2$, C≡CH, COOH, CHO, imidoester, haloacetyl, hydrazide, alkoxyamine, aryl azide, diazirines, maleimide, carbodiimide, N-hydroxysuccinimide (NHS), thiazolidine-2-thione, pyridyldisulfide, difluorinatedcyclooctyne, Staudinger reagent pairs, isocyanate, isothiocyanate, thioether, sulfhydryl, hydrazine, hydroxymethyl phosphine, sulfo-NHS ester, pentafluorophenyl ester, sulfonylazide, and 5H-dibenz[b,f] azepine and their derivatives.

N-Oxide Copolymers: Hydrophobic and Hydrophilic Constitutional Units.

In further aspects, the invention provides N-oxide copolymers that include N-oxide repeating units and hydrophobic and/or hydrophilic constitutional units.

In certain embodiments, the copolymer is a random, diblock, or hyperbranched copolymer that includes N-oxide repeating units (e.g., poly(N-oxide)).

Representative block copolymers include at least one N-oxide component block (A); and at least one hydrophobic block (B). In certain embodiments, the copolymer further comprises a hydrophilic block (C) or a second hydrophobic block (C). Block copolymers of the invention include AB diblock copolymers, ABC triblock copolymers, ABA triblock copolymers, BAB triblock copolymers, linear or star-shape multiblock (AB)$_n$ copolymers, Miktoarm block copolymers (AB$_n$ or A$_n$B), and mixtures thereof. In certain embodiments, the copolymer further comprises neutral hydrophilic repeating units (e.g., alkylene oxide repeating units, such as ethylene oxide repeating units).

In certain embodiments, the copolymer includes an N-oxide component that comprises a repeating unit derived from a N-oxide monomer (e.g., an N-oxide monomer of the invention having formulae (I) or (II), and a hydrophobic component that comprises a repeating unit derived from a hydrophobic monomers.

Representative hydrophobic repeating units may be derived from acrylic acids and esters, alkyl acrylic acids and esters, acrylamides, alkyl acrylamides, polysiloxane repeating units, polyester repeating units, polyurethane repeating units, polystyrene repeating units, and fluorinated derivatives thereof.

In certain embodiments, the copolymer includes an N-oxide component that comprises repeating units derived from a N-oxide monomer (e.g., an N-oxide monomer of the invention having formulae (I) or (II)), a hydrophilic component that comprises repeating units derived from a hydrophilic monomer, and optionally a hydrophobic component that comprises repeating units derived from a hydrophilic monomer. In certain of these embodiments, the hydrophilic repeating units comprise N-oxide moieties. In other embodiments, the hydrophilic repeating unit can be a polyhydroxyethylmethacrylate (PHEMA), polyethylene glycol (PEG), polycarboxybetaine (PCB), polysulfobetaine (PSB), poly-phosphobetaine (PPB), polyphosphorylcholine (PPC), polyacrylamide (PAA), poly(2,3-dihydroxypropyl methacrylate) (PDHPM), poly(N-isopropylacrylamide) (PNIPAM), polyacrylamide (PAM), poly(2-oxazoline), poly(acrylic acid), polymethacrylate (PMA), poly(vinyl alcohol) (PVA), poly(vinylpyrrolidone) (PVP), polyelectrolyte, polysaccharide, polyamide, and miscellaneous hydrophilic polymers, peptide-based materials and copolymers of two or more hydrophilic monomers.

Silicone-Based N-Oxide Copolymers.

In other aspects, the invention provides silicone-based N-oxide copolymers that include N-oxide repeating units and silicone repeating units ($[R_1R_2SiO]_n$).

In certain embodiments, the silicon-based copolymer includes a poly(N-oxide).

In certain embodiments, the silicon-based copolymer is a block copolymer that includes a poly(N-oxide).

In other embodiments, the silicon-based copolymer is a graft copolymer that includes a poly(N-oxide).

Suitable silicone-based N-oxide copolymers include silicone repeating units that have the formula $[R_1R_2SiO]_n$, where $R_1$ and $R_2$ are organic groups such as alkyl (methyl, ethyl), phenyl, vinyl, hydride, silanol, alkoxy/polymeric alkoxide, amine, epoxy, carbinol, methacrylate/acrylate, mercapto, acetoxy/chlorine/dimethylamine and other organic groups.

In certain embodiments, the block copolymers have a poly(N-oxide) block (PNO) that can be grown from silicone, for example, by living polymerization using polydimethylsiloxane (PDMS) and a macroinitiator. Representative silicone-based N-oxide block copolymer include PNO-b-PDMS diblock, PNO-b-PDMS-b-PNO triblock, PDMS-b-PNO-b-PDMS triblock, PDMS-b-PEG-PNO triblock, linear or star-shape multiblock $(PDMS-b-PNO)_n$, Miktoarm block $(PDMS)_m$—$(PNO)_n$, or comb-like PDMS—$(PNO)_n$ copolymers.

For comb-like PDMS—$(PNO)_n$ copolymers, the poly(N-oxide) polymer chain can be grafted from the PDMS backbone. This can be achieved by using PDMS-based multi-initiator (i.e., initiators are attached on the side of PDMS backbone). For "graft-to" methods, poly(N-oxide) polymer chain with functional end group reacted with PDMS backbone can also produce comb-like graft copolymers.

For graft copolymers, the N-oxide side chain can be attached to the silicone backbone using thiol-ene chemistry, Michael addition, hydrosilylation reaction, electrophilic addition, nucleophilic addition, or other suitable reaction.

As noted above, the block copolymers can be prepared by living polymerization methods. Representative useful living polymerization methods include living anionic polymerization, living α-olefin polymerization, living cationic polymerization, living ring-opening metathesis polymerization, living free radical polymerization, living chain-growth polycondensations, living group-transfer polymerization, and table free radical mediated polymerization (SFRP), atom transfer radical polymerization (ATRP), reversible addition-fragmentation chain transfer (RAFT) polymerization.

In further aspects, the invention provides a bulk material or a coating composition that includes (a) a silicone-based N-oxide copolymer and (b) a polymeric matrix, wherein the polymeric matrix comprises a polymer selected from the group consisting of rosins, acrylic polymers, polyesters, amino resins, polyurethanes, polyamides, polyimides, epoxy and phenolic resins, alkyd resins, polyphosphazenes, polysiloxanes, fluorinated polymers, polysiloxane modified by N-oxide, zwitterionic (sulfobetaine, carboxybetaine, protected carboxybetaine, and MPC), amides, PEG, poly(2-oxazoline), PVA, polysaccharide, or mixtures thereof.

In certain embodiments, the bulk material or coating composition comprises a polysiloxane binder matrix modified by N-oxide (formed from a silicone-based N-oxide copolymer). These materials and coatings may further comprise a polysiloxane binder matrix modified by zwitterionic (sulfobetaine, carboxybetaine, protected carboxybetaine, and MPC), amides, PEG, poly(2-oxazoline), PVA, polysaccharide or their combinations.

In certain embodiments, the bulk material or coating composition comprises (a) a copolymer (diblock, triblock, graft or random) comprising hydrophobic (e.g., PDMS) and hydrophilic (e.g., N-oxide, zwitterionic, protected zwitterionic, PEG, amide, poly(2-oxazoline), PVA, polysaccharide or their combinations) and (b) a polymeric matrix as described above.

The bulk material and coating composition may each further comprise one or more active ingredients, such as a biocide or an enzyme.

N-Oxide Polymeric Surface Coatings, Bulk Materials, and Stand-Alone Materials

In other aspects, the present invention provides N-oxide polymeric surface coatings, bulk materials, and stand-alone materials. In certain embodiments, the N-oxide polymeric surface coatings, bulk materials, and stand-alone materials are prepared from N-oxide monomers and polymers and copolymers prepared from N-oxide monomers.

N-oxide polymers can be attached to surfaces (e.g., medical devices, sensors, membranes, ships and marine structures) via "graft-from" or "graft-to" methods to render the surfaces nonfouling. N-oxide polymers can be also blended with or into bulk materials (e.g., silicone). Surface coating can be on flat or nano/micro-particle surfaces. N-oxide polymers can also be prepared into stand-alone low-fouling and high-strength materials and devices for medical and marine applications via (i) unique backbones such as silicone, fluorinated, urethane, imide, amide and (ii) strong interactions such as multiple hydrogen bonds, and (iii) interpenetrating networks.

N-Oxide Polymeric Surface Coatings.

The present invention provides N-oxide polymeric surface coatings. In certain embodiments, the surface coating comprises a N-oxide polymer (oligomer) or N-oxide copolymer of the invention as described herein (e.g., a polymer of formulae (III), (IV), (V), or (VI)).

The surfaces coated with the N-oxide polymers and copolymers have nonfouling properties. Nonfouling properties of the surfaces can be evaluated by fibrinogen adsorption and cell adhesion. In certain embodiments, surfaces of the invention have fibrinogen adsorption less than about 200 ng/cm$^2$. In other embodiments, surfaces of the invention have fibrinogen adsorption less than about 100 ng/cm$^2$. In further embodiments, surfaces of the invention have fibrinogen adsorption less than about 50 ng/cm$^2$. In other embodiments, surfaces of the invention have fibrinogen adsorption less than about 30 ng/cm$^2$. In further embodiments, surfaces of the invention have fibrinogen adsorption less than about 20 ng/cm$^2$. In other embodiments, surfaces of the invention have fibrinogen adsorption less than about 10 ng/cm$^2$. In certain embodiments, surfaces of the invention have fibrinogen adsorption less than about 5 ng/cm$^2$.

The preparation and nonfouling properties of a surface coated with a representative N-oxide polymer of the invention are described in Example 2.

In certain embodiments, the surfaces are coated with a N-oxide polymer or copolymer prepared from one or more N-oxide monomers selected from the polymerizable groups comprising of, but not limited to N-oxide acrylates, N-oxide acrylamides, N-oxide methacrylates, N-oxide methacrylamides, N-oxide vinyl compounds, N-oxide epoxides and mixtures thereof. Representative N-oxide monomers include those described herein, including N-oxide monomers of formula (I) and formula (II).

In certain embodiments, the N-oxide polymer or copolymer is a random, a multiblock, or a hyperbranched copolymer comprising a poly(N-oxide). In other embodiments, the N-oxide polymer or copolymer is an interpenetrating N-oxide polymer network.

In certain embodiments, the N-oxide polymer or copolymer is has surface adhesive groups (e.g., DOPA, thiol, silane, click chemistry, hydrophobic, hydrophilic, and charged groups).

The surfaces coated with the N-oxide polymers and copolymers can be prepared by attaching the N-oxide polymer or copolymers to a substrate surface via covalent interactions, physically hydrophobic-hydrophobic, charge-charge, and hydrogel-bonding interactions, or their combinations of chemical and physical interactions.

The surface coated with the N-oxide polymers or copolymers can be prepared by grafting the N-oxide polymers from the substrate surface ("grafted from") (e.g., preparing the polymeric surface by forming the polymer or copolymer by polymerizing suitable monomers in the presence of the substrate, see Example 2) or can be prepared by grafting the N-oxide polymers to the substrate surface ("grafted to") (e.g., preparing the polymeric surface by coupling the pre-formed polymer or copolymer to the substrate).

In certain embodiments, the N-oxide polymers and copolymers are grafted from the substrate by polymerization methods, such as atom-transfer radical-polymerization (ATRP), reversible addition-fragmentation chain-transfer polymerization (RAFT), or photoinferter polymerization.

In certain embodiments, the N-oxide polymers and copolymers are grafted to the substrate by conjugation methods, such as click chemistry, DOPA conjugation chemistry, or self-assembled monolayer (SAM) via thiol or silane.

The N-oxide polymeric surface coatings can be applied to a variety of substrates (e.g., substrate surfaces). In certain embodiments, the surface is all or part of biomedical device. Representative biomedical devices include catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

In certain embodiments, the device is a contact lens.

In certain embodiments, the surface is all or part of a particle. Representative particles include metal, metal oxide, ceramic, synthetic polymer, natural polymer, silicon dioxide, crystal, and semiconductor material particles. In certain embodiments, the particle is a biomolecule, such as a protein (e.g., an enzyme) or a nucleic acid (e.g., a DNA or a RNA). In other embodiments, the particle is a cell.

In certain embodiments, the surface is all or part of a membrane or a bio-separation membrane. Representative membranes include membranes used for protein purification, wastewater treatment, bioreactors, desalination of sea water, and water/oil purification.

In certain embodiments, the device is a marine device. All or part of the surface of the marine device can be coated with the polymeric N-oxide coating. Representative marine devices include marine products, such as marine vessel hulls, marine structures, bridges, propellers, heat exchangers, periscopes, sensors, fish nets, cables, tubes/pipes, containers, membranes, and oil booms.

In certain embodiments, the surface is on or forming all of a drug delivery vehicle, such as a gene delivery vehicle, an RNA delivery vehicle, or a protein delivery vehicle.

In certain embodiments, the surface is on or forming all or part of an implantable or subcutaneous sensor.

In certain embodiments, the surface is on or forming all or part of a tissue scaffold.

N-Oxide Polymeric Bulk Materials.

The present invention provides N-oxide polymeric bulk materials. In certain embodiments, the bulk materials comprises a N-oxide polymer (oligomer) or N-oxide copolymer of the invention as described herein (e.g., a polymer of formulae (III), (IV), (V), or (VI)). In certain embodiments, the materials are prepared by a polymerizing or copolymerization process using a monomer of the invention as described herein (e.g., a monomer of formula (I) or (II)).

In certain embodiments, the bulk material is obtained by blending of one or more N-oxide polymers or copolymers with one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

In other embodiments, the bulk material comprises an interpenetrating N-oxide polymer network and one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

N-Oxide Polymeric Standalone Materials.

The present invention provides N-oxide polymeric standalone materials. In certain embodiments, the materials comprise a N-oxide polymer (oligomer) or N-oxide copolymer of the invention as described herein (e.g., a polymer of formulae (III), (IV), (V), or (VI)). In certain embodiments, the materials are prepared by a polymerizing or copolymerization process using a monomer of the invention as described herein (e.g., a monomer of formula (I) or (II)).

In certain embodiments, the N-oxide polymeric standalone materials are nonfouling materials and have high mechanical strength. In certain of these embodiments, the standalone material is a nonfouling material having protein adsorption less than about 30, less than about 50, or less than about 100 ng/cm$^2$, having tensile/compressive strengths greater than about, 0.2, greater than about 0.5, or greater than about 1.0 MPa.

In certain embodiments, the N-oxide polymeric standalone material is a N-oxide polymer network that is reinforced by introducing (a) dipole-dipole interactions such as cyano groups (C≡N) and (b) hydrogen donors/acceptors such as amide group (—(NH)—(C=O)—), multiple amide groups ((—(NH)—(C=O)—)$_n$ (n=1-5)), urethane group (—(NH)—(C=O)—O—), multiple urethane groups ((—(NH)—(C=O)—O—)$_n$ (n=1-5)), urea group (—(NH)—(C=O)—(NH)—), multiple urea groups ((—(NH)—(C=O)—(NH)—)$_n$ (n=1-5)), and their combinations. These groups can be derived from N-oxide monomers and N-oxide (random- or block-) copolymers. These groups can be in the polymer backbone or polymer pendant group.

The N-oxide polymer networks can be reinforced with backbones in a N-oxide monomer or a N-oxide polymer, such as polyacrylate, polymethacrylate, polyacrylamide, polymethacrylamide, polyamide, polydimethylsiloxane, polyethylene, polypropylene, polystyrene, polytetrafluoroethylene, polyisobutene, polyesters, polycarbonates, polyurethanes, polyureas, polysulfides, polysulfones, polyimides, polyepoxies, polyanhydrides, polyethers, and other condensation/addition polymers. In certain embodiments, the N-oxide polymer network is reinforced by any combination of the above.

In certain embodiments, the N-oxide polymer can be form copolymers with other polymers or composites, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers. Fiber, clays, nanotubes and other inorganic objects can be added to increase mechanical properties of these materials.

The N-oxide standalone materials of the invention can be formed into an object by a variety of methods, such as injection molding, blow molding, extrusion molding, calendaring molding, flow casting, compression molding, prevarication molding, and 3D printing.

The N-oxide standalone materials of the invention can be used in biomedical/biotechnological, consumer product, engineering/marine, therapeutics/diagnostics applications such as catheters, ear drainage tubes, feeding tubes, glaucoma drainage tubes, hydrocephalous shunt, keratoprosthesis, nerve guidance tubes, tissue adhesive, x-ray guide, an artificial joint, artificial heart valve, artificial blood vessel, pacemaker, left ventricular assist device (LVAD), artery graft, vascular grafts, stent, intravascular stent, cardiac valves, joint replacements, blood vessel prostheses, skin repair devices, cochlear replacements, contact lenses, artificial ligaments and tendons, dental implants and tissue scaffolds for regenerative tissue engineering, drug delivery, gene delivery, RNA delivery, protein delivery, marine and engineering devices/objects (e.g., membranes, tubes, pipes, containers, or plates).

In certain embodiments, the standalone materials can be used in marine products such as marine vessel hulls, marine structures, bridges, propellers, heat exchangers, periscopes, sensors, fish nets, cables, tubes/pipes, containers, membranes, and oil booms.

In certain embodiments, the standalone materials can be conjugated to a biomaterial. Representative biomaterials include nucleic acids (e.g., a gene, DNA, RNA), proteins (e.g., enzymes, antibody or functional fragment thereof), peptides, lipids, cells or microorganisms, solid nanoparticles (iron oxide, silica, quantum dot or gold nanoparticles), or used for protection against dehydration on skin by surfactants.

N-Oxide Polymeric Hydrogels

The present invention provides N-oxide polymeric hydrogels. In certain embodiments, the hydrogel comprises a crosslinked N-oxide polymer (oligomer) or N-oxide copolymer of the invention as described herein (e.g., a polymer of formulae (III), (IV), (V), or (VI)). In certain embodiments, the hydrogel is prepared by a polymerizing or copolymerization process using a monomer of the invention as described herein (e.g., a monomer of formula (I) or (II)).

N-oxide polymeric hydrogels can be created from N-oxide monomers and various crosslinkers, including degradable or non-degradable N-oxide crosslinkers. N-oxide star polymers can be prepared by forming hydrogels (e.g., via click chemistry). These hydrogels can be in the form of bulk hydrogels or pellet hydrogels. These hydrogels can be used as implantable materials and devices to reduce capsule formation and as media to protect, expand, preserve and differentiate various cells (e.g., stem cells, immune cells, islets, platelets and cardiomyocytes) in controlled manners. Pellet and star hydrogels can be injectable along with biologics (e.g., various cells and tumor for tumor vaccine).

In certain embodiments, the N-oxide hydrogel is a crosslinked hydrogel prepared from one or more N-oxide monomers (e.g., a monomer of formula (I) or (II)) using one or more crosslinkers.

In certain of these embodiments, the crosslinker is a N-oxide based crosslinker. Representative N-oxide crosslinkers include those of formula (VII):

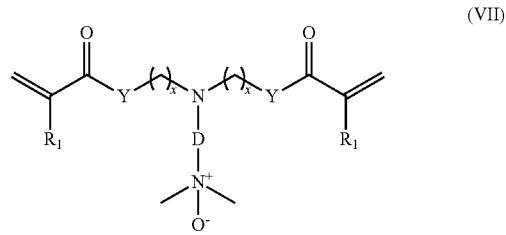

wherein
$R_1$ is independently selected from H, —$(CH_2)_x$—$CH_3$ (x=0-4), and CN;
x is an integer from 1 to 200;
Y is O or NH; and
D is —$C(=O)(CH_2)_n$— or —$(CH_2)_n$—, where n is an integer from 1 to 20.

In other of these embodiments, the crosslinker is a multifunctional zwitterionic crosslinker that includes carboxybetaine, sulfobetaine, or phosphobetaine moieties.

In further of these embodiments, the crosslinker is a multifunctional crosslinker, such as N,N'-methylenebisacrylamide (MBAA), polyethylene glycol (PEG) diacrylate or diacrylamide, or PEG dimethacrylate or dimethacrylamide.

In certain embodiments, the hydrogel is prepared using a bifunctional N-oxide crosslinker. In other embodiments, the hydrogel is prepared using a degradable or non-degradable crosslinker. In further embodiments, the hydrogel is prepared using a degradable, zwitterionic disulfide crosslinker. In other embodiments, hydrogel is prepared using peptide based crosslinker that can be degraded by enzymes or suitable agents.

The N-oxide hydrogels of invention can be prepared by free radical mediated polymerization techniques, such as thermo-, photo-, or redox.

The preparation of a representative N-oxide hydrogel of invention is described in Example 3. Protein adsorption and cell adhesion to the representative N-oxide hydrogel is described in Example 4.

The N-oxide hydrogels of invention can be used for biosensors and biomedical devices, vascular grafts, intravascular stents, cardiac valves, joint replacements, cell preservation/expansion/differentiation, drug delivery platforms, ship hulls, marine structures/equipment, and other materials and devices that come into contact with physiological environments.

In certain embodiments, the N-oxide hydrogel is a star hydrogel. Star hydrogels can be prepared from a polymer having a core and a plurality of N-oxide based or zwitterionic branches covalently coupled to the core. Representative cores include one of a small molecule, oligomer, or polymer of or star shapes with three, four, five or more branches.

In certain embodiments, the hydrogel is crosslinked by a degradable crosslinker that can be selectively degraded (i.e., under specific conditions). The degradable crosslinker can be selected from peptide crosslinkers, polysacharride crosslinkes, anhydride crosslinkers, dissulfide crosslinkers, and polyester crosslinkers. For certain of these embodiments, the hydrogel can be hydrolyzed or digested by enzymes.

In certain embodiments, the star hydrogel branch polymer comprises terminal functional groups bound to the terminal end of the branches (e.g., terminal end of plurality of N-oxide or zwitterionic branches). Representative terminal functional groups include OH, NH, $NH_2$, SH, $N_3$, $CH=CH_2$, $C\equiv CH$, COOH, CHO, imidoester, haloacetyl, hydrazide, alkoxyamine, aryl azide, diazirine, maleimide, carbodiimide, N-hydroxysuccinimide (NHS), thiazolidine-2-thione, pyridyldisulfide, difluorinatedcyclooctyne, Staudinger reagent pairs, isocyanate, isothiocyanate, thioether, sulfhydryl, hydrazine, hydroxymethyl phosphine, sulfo-NHS ester, pentafluorophenyl ester, sulfonylazide, and 5H-dibenz[b,f]azepine.

In certain embodiments, the hydrogel comprises a first polymer/copolymer (first star hydrogel) bound to one or more second polymer/copolymers (second star hydrogel). The hydrogel can be used as an injectable hydrogel. In certain of these embodiments, the first polymer is bound to the one or more second polymers by a terminal functional group.

The star hydrogel can be combined with zwitterionic hydrogels and formed as a pellets of various size in specific templates or through mechanical reduction (e.g., blender). These pellet hydrogels can be used as injectable hydrogels with or without biological contents.

The N-oxide star hydrogels of the invention can be made by (a) synthesizing N-oxide or zwitterionic branches by ATRP, RAFT, ROP, condensation, Michael addition, branch generation/propagation reaction, and (b) reacting the N-oxide or zwitterionic branches with a core to provide the star polymer. In certain embodiments, the method further comprises functionalizing the terminal end of the N-oxide or zwitterionic branches by "click" reaction, thiol exchange reaction, or reductive reaction.

In certain embodiments, the N-oxide hydrogel is a microgel. The microgels of the invention are micron-scale, crosslinked hydrogels having dimensions between about 1 micron ($10^{-6}$ m) and 1 mm ($10^{-2}$ m) composed of N-oxide based monomers and supported by any crosslinking chemistry.

Microgels of the invention can be prepared by a variety of methods using a functionalized N-oxide monomer, oligomer, or polymer, in which:

(a) one of a reactive pair selected from an azide and an alkyne, an azide and an alkene, a thiol and a maleimide, a thiol and an alkene, a thiol and a disulfide, or any other "click", bioorthogonal, or other reactive pair;

(b) positioned at the terminus of the polymeric structure(s) or along the backbone;

(c) integrates a peptide, nucleic acid, protein, antibody, nanoparticle, microparticle, micelle, liposome, polymersome, drug, drug precursor, or other therapeutic species or drug delivery modality, for surgical applications, therapeutic applications, wound-healing applications, drug delivery formulations, cell storage and preservation, or regenerative medicine.

In certain embodiments, the microgel comprises a mixture of N-oxide monomers or polymers and other classes of ionic or non-ionic nonfouling monomers or polymers, or a copolymer of N-oxide based polymers and other classes of ionic or non-ionic monomers.

For the microgels, crosslinking is achieved using any combination of physical and/or chemical mechanisms, which in certain embodiments include:

(a) chemical crosslinkers of any structure that are copolymerized with the monomers via a radical-mediated reaction, including commercially available crosslinkers based on polyethylene glycol (PEG), oligoethylene glycol (OEG) or other structures or groups, terminated with two or more acrylate, methacrylate, acrylamide, maleimide or similar reactive groups, or custom synthesized crosslinkers incorporating any functional, reactive, or degradable groups. Optional degradable groups may be selected from disulfide bonds, esters, anhydrides, enzymatically cleavable peptides (such as the GPQGIWCG motif), or chemistries responsive to external stimuli;

(b) bioorthogonal crosslinking chemistries and 'click' chemistries, such as azide/alkyne (including SPAAC) and thiol-ene chemistries, whether through inclusion as functional groups in the main polymer chain(s) or architectures or as separate crosslinking molecules;

(c) physical interactions of any type including ionic interactions, hydrogen bonding, hydrophobic interactions, interactions with biomolecules or nanoparticles of a natural or synthetic origin, or any other reversible or nonreversible physical interactions; and (d) any combination of the crosslinking mechanisms noted above.

In certain embodiments, the microgel is prepared using bifunctional N-oxide crosslinking molecule, oligomer or polymer incorporating one or more N-oxide moieties or a mixture of these molecules.

In certain embodiments, the microgel is prepared using zwitterioinic (carboxybetaine, sulfobetaine or phosphobetaine) crosslinking molecule, oligomer or polymer incorporating one or more zwitterionic moieties or a mixture of these molecules. These crosslinkers may incorporate degradable groups, such as disulfide bonds, esters or stimuli-responsive groups or degradable peptides.

In certain embodiments, the invention provides a material formed from two or more assembled microgels, as described above, wherein the interactions between each discrete microgel result in bulk material with unique properties. These materials can include other ingredients, such as small molecule drugs, peptides, biomolecules, nanoparticles, cells or tissues.

In certain embodiments, the microgels and assemblies described above are produced from microgels having finite dimensions as a result of the polymerization method, for example, microemulsion polymerization.

In other embodiments, the microgels are derived from the (bulk) hydrogels described above or the star hydrogels described above, further sized to a finite dimension after polymerization, using any processing step to grind, extrude, mince, cut, or pellet the hydrogels to discrete units of finite size.

The microgels and assemblies described above can be dried or lyophilized (freeze-dried) to a dehydrated powder for storage, transport, use, or sterilization. The microgel powder can be rehydrated with any aqueous fluid, including water, saline or ionic solutions, cell growth or preservation media containing or not containing cells, or any other physiologically relevant solution that may contain therapeutic drugs, therapeutic proteins, therapeutic nucleic acids, cells, nanoparticles, or microparticles.

The N-oxide star hydrogels and microgels and their assemblies and/or partially or fully dried or rehydrated compositions of these, have the following uses:

(a) materials with non-Newtonian behavior (e.g., that exhibits viscoelastic, rheopectic, thixotropic, shear thickening (dilatant), shear thinning (pseudoplastic), and/or Bingham plastic properties);

(b) self-healing materials and/or shape memory materials, or similar classes of 'smart' materials that can repair damage or recover their properties after damage or external stimuli; and (c) antifouling materials or surface coatings to prevent nonspecific protein or other biomolecule adsorption, e.g., for marine applications, drug delivery platforms, biosensors and other medical devices, vascular grafts, intravascular stents, cardiac valves, joint replacements, and other materials and devices that come into contact with physiological environments.

The N-oxide star hydrogels and microgels and their assemblies can be used as an injectable or spreadable material for biomedical applications, particularly in applications requiring non-Newtonian fluid properties and high biocompatibility:

(a) injectable or spreadable materials capable of mechanical support, such as those used in cosmetic or reconstructive surgery, blood vessel prostheses, skin repair devices, cochlear replacements, injectable vitreous substances, artificial cartilage, artificial fat, collagen-mimics and other soft tissue-mimics or supports;

(b) injectable or spreadable materials with desirable or specific biological interactions with a surface or tissue, particularly when nonspecific interactions should be avoided or a desired balance of nonspecific/specific interactions must be achieved; and (c) injectable or spreadable carriers to deliver and/or protect or shield drugs, biomolecules (e.g., nucleic acids, peptides, proteins, polysaccharides), cells (e.g., pancreatic islets, cardiovascular cells, stem cells, T cells, blood cells), nanoparticles or microparticles (e.g., PLGA/drug formulations), micelles, liposomes, polymersomes, or other therapeutic species or drug delivery modalities, for surgical applications, therapeutic applications, wound healing, and drug delivery formulations.

The N-oxide star hydrogels and microgels and their assemblies can be used as a scaffold, matrix, or substrate for the growth, maintenance or expansion of cells and tissues, in which the cells and microgel constructs can be grown using any culture method or apparatus including any type of bioreactor, and can be derived from lineages including:

(a) pluripotent and multipotent stem and progenitor cells, including:
  (i) embryonic stem cells (ESCs), tissue-derived stem cells (e.g., from skin, blood, or eye), hematopoietic stem and progenitor cells (HSPCs) derived or purified from umbilical cord blood or bone marrow, mesenchymal stem cells, or induced pluripotent stem cells (iPSCs),
  (ii) genetically modified or transfected stem and progenitor cells, and
  (iii) cancer stem cells (CSCs);

(b) hematopoietic cells typically circulating in human blood, including red blood cells (erythrocytes), white blood cells (leukocytes) and platelets (thrombocytes);

(c) immune cells and progenitors or differentiated lineages thereof, including:
  (i) T cells expressing the CD8 surface glycoprotein, particularly including naïve cytotoxic T lymphocytes (CTLs) and differentiated or activated lineages thereof including central memory T cells,
  (ii) T cells expressing the CD4 surface glycoprotein particularly including naïve helper T lymphocytes, and differentiated or activated lineages thereof including TH1, TH2, TH9, TH17, TFH, Treg and central memory (TCM) T cells,
  (iii) regulatory T cells (TREG) from any source, either natural Tregs or induced Tregs,
  (iv) natural killer T cells (NKT) cells,
  (v) chimeric antigen receptor T cells (CAR-T),
  (vi) genetically modified T cells;

(d) B cells, dendritic cells, and other antigen-presenting cells (APCs) or immune cells not specifically listed above;

(e) pancreatic islet or other insulin-producing cells and 3 cells useful in the treatment and management of diabetes;

(f) nervous system cells and progenitors;

(g) cardiovascular system cells and progenitors; and (h) cells useful in the fields of immunotherapy, regenerative medicine, hematologic diseases or malignancies, or cancer vaccines or treatments.

The N-oxide star hydrogels and microgels and their assemblies can be used as a biocompatible material, scaffold, formulation component or contacting material for any method of preserving cells or tissues or retaining their biological function for clinical or military utility, particularly for cell types that are difficult to preserve with conventional methods such as blood cells (e.g., platelets and red blood cells) for extended time periods, at room or low temperatures, in whole blood or preservation solutions, and with or without the presence of DMSO, glycerol, glycine betaine or other osmolytes or cryoprotectants.

Platelet preservation using a representative N-oxide polymer pellet microgel is described in Example 5.

The N-oxide star hydrogels and microgels and their assemblies can be used for objects, devices, and components such as implantable biosensors; wound care devices, glues and selants, a contact lens; a dental implant; an orthopedic device such as an artificial joint, an artificial bone, an artificial ligaments, and an artificial tendon; a cardiovascular device such as a cathether, an artificial valve, an artificial vessel, an artificial stent, LVADs, or a rhythm management device; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; animplanted biosensor; an access port device; and a tissue scaffold pulmonic devices such as valves for management of COPD or artificial lungs; radiology devices such as radio-opaque or sono-opaque markers; or urology devices such as catheters or artificial urethrae.

In other aspects, the invention provides a substrate coated with a N-oxide star hydrogel or microgel or microgel assemblies. Representative substrates include objects, devices, and components such as implantable biosensors; wound care devices, glues and selants, a contact lens; a dental implant; an orthopedic device such as an artificial joint, an artificial bone, an artificial ligaments, and an artificial tendon; a cardiovascular device such as a cathether, an artificial valve, an artificial vessel, an artificial stent, LVADs, or and a rhythm management device; gastroenterology devices such as feeding tubes, alimentary canal clips, gastro-intestinal sleeves, or gastric balloons; OB/Gyn devices such as implantable birth control devices or vaginal slings; nephrology devices such as anastomotic connectors or subdermal ports; neurosurgery devices such as nerve guidance tubes, cerebrospinal fluid drains or shunts, dermatology devices such as skin repair devices an ophthalmic device such as a shunt, otorhinolaryngology devices such as stents, cochlear implants, tubes, shunts or spreaders, an intra-ocular lense; an aesthetic implant such as a breast implant, a nasal implant, and a cheek implant; a neurologic implant such as a nerve stimulation device, a cochlear implant, and a nerve conduit; a hormone control implant such as a blood sugar sensor and an insulin pump; an implanted biosensor; an access port device; and a tissue scaffold pulmonic devices such as valves for management of COPD or artificial lungs; radiology devices such as radio-opaque or sono-opaque markers; or urology devices such as catheters or artificial urethrae.

N-Oxide Polymeric Nanoparticles and Microparticles

In another aspect, the invention provides nano- and microparticles comprising the N-oxide polymers and copolymers of the invention. The N-oxide polymers and copolymers of the invention can be used to form nano- and microparticles in the form of nano- and microgels, micelles, liposomes, and polymersomes. They also can be used to coat solid particles such as quantum dots, iron oxides, silica, and gold for therapeutics or diagnostics. The N-oxide polymers and copolymers of the invention can be associated with nano- and microparticles by covalent as well as non-covalent attachment.

In certain embodiments, particles having nanoscale dimensions are provided. The particles have a core having a surface having a plurality of N-oxide polymers or copolymers grafted thereto or grafted therefrom. Representative particle cores include a metal, a metal oxide, a ceramic, a synthetic polymer, a natural polymer, a crystal, a semiconductor material, a graphene, a graphene oxide, an iron oxide, a silica, a quantum dot, a hydrogel, a liposome, a micelle, a carbon-based material, or a biomolecule.

N-Oxide Polymer and Copolymer Conjugates

In a further aspect, the invention provides N-oxide polymer and copolymer conjugates. The N-oxide polymers can be attached to biomolecules (e.g., proteins/peptides, nuclear acids, and sugars), other macromolecules, and cells by graft-to or graft-from methods top provide a variety of conjugates.

In certain embodiments, the N-oxide polymer conjugate or copolymer conjugate is a N-oxide polymer bioconjugate comprising one or more N-oxide polymers coupled to a biomolecule. Suitable biomolecules include proteins, nucleic acids, glycoproteins, proteoglycans, and lipids. Suitable biomolecules include small molecule therapeutic agents (i.e., carbon-based therapeutic agents having a molecular weight less than about 1000 g/mole, preferably less than about 800 g/mole).

Representative proteins include enzymes, signaling proteins, hemostasis and thrombosis proteins, vaccines, complement system proteins, and antibodies, their functional fragments or characteristic portions. Representative signaling proteins includes hormones, cytokines, regulatory proteins, insulins, and PD-1/PD-L1/2 inhibitors.

In other embodiments, the N-oxide polymer conjugate or copolymer conjugate is a N-oxide polymer or copolymer bioconjugate comprising one or more N-oxide polymers coupled to a cell, a virus, or a bacterium.

The N-oxide polymer conjugate or copolymer conjugate may be a delivery vehicle. Representative deliver vehicles include micelles, liposomes, or polymersomes, for therapeutic or diagnostic applications.

In certain embodiments, the invention provides a micelle, a liposome, a polymersome, or a particle that is self-assembled from a copolymer or a conjugated lipid of the invention comprising one or more N-oxide polymers or copolymers.

In a further embodiment, the invention provides a composition comprising a N-oxide polymer or copolymer conjugate and a pharmaceutically accepted carrier or diluent. In certain embodiments, the N-oxide polymer and copolymers of the invention can be used as carrier or diluent for compositions.

The preparation of a representative N-oxide polymer protein conjugate is described in Example 6. The immunogenicity of a representative N-oxide polymer protein conjugate is described in Example 7.

N-Oxide Polymer Nanogels and Nanocages

In another aspect, the invention provides N-oxide polymer nanogels and nanocages. The N-oxide polymers can be used to provide nanogels that chemically trap one or more other species, and nanocages that physically trap one or more other species.

In certain embodiments, the invention provides a nanogel for chemically encapsulating cargo, comprising one or more N-oxide polymers or one or more N-oxide copolymers.

In other embodiments, the invention provides a nanocage for physically encapsulating cargo, comprising one or more N-oxide polymers or one or more N-oxide copolymers.

Suitable cargo (e.g., species) that are chemically trapped by a nanogel or physically trapped by a nanocage include biomolecules, such as proteins, lipids, glycoprotein, cells, viruses, bacteria, and small molecules (e.g., therapeutic agents having molecular weights less than about 1000 g/mole, preferably 800 g/mole), or other biomolecules as described herein.

In certain embodiments, the nanogel or nanocages comprise a N-oxide polymer or copolymer and one or more therapeutic agents.

In other embodiments, the nanogel or nanocage comprise a N-oxide polymer or copolymer and one or more diagnostic agents.

In further embodiments, the nanogel or nanocage comprises a N-oxide polymer or copolymer, one or more therapeutic agents, and one or more diagnostic agents.

The preparation of a representative N-oxide polymer nanocage for protein encapsulation is described in Example 8. Protein stabilization of a representative N-oxide polymer nanocage is described in Example 9 and illustrated in FIG. 7.

Figure 8:
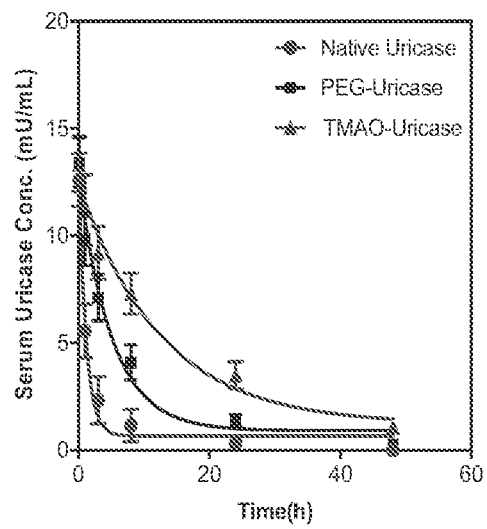
FIG. 8 compares blood circulation profiles of native uricase, PEG-uricase, and a representative N-oxide polymer-nanocage-protected uricase (TMAO-uricase).

Pharmacokinetics of proteins with a representative N-oxide polymer nanocage is described in Example 10 and illustrated in FIG. 8.

Ectoine Monomers, Polymers, Copolymers and their Uses

Ectoine (1,4,5,6-tetrahydro-2-methyl-4-pyrimidine carboxylic acid) is a pyrimidine derivative where all except one double bond have been hydrogenated. An important characteristic of this molecule is the delocalized it-bonding in the N—C—N group which results in a permanent zwitterionic structure. As described herein, this zwitterionic property of ectoine can be exploited to make zwitterionic materials. As described herein, the ectoine monomers can be readily polymerized under standard polymerizing conditions to form poly(ectoines). These polymers can be linear, branched or crosslinked, and are able to withstand nonspecific biofouling and provide strong hydration in different manners.

Ectoine Monomers, Polymers, Copolymers and their Uses

The present invention provides ectoine monomers, ectoine polymers and copolymers, methods for making the ectoine monomers, polymers, and copolymers, compositions and materials that include ectoine polymers and copolymers, and methods for using the ectoine polymers and ectoine copolymers.

As described herein, the ectoine monomers can be readily polymerized under standard polymerizing conditions to provide ectoine polymer and copolymers.

In one aspect, the invention provides polymerizable ectoine monomers and its precursors.

In certain embodiments, the ectoine monomers have formula (VIIIA) and the ectoine monomer precursors have formula (VIIIB):

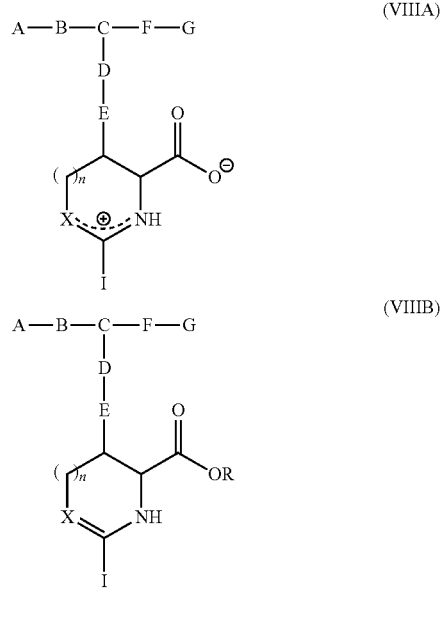

wherein

A is independently selected from H, F, Cl, Br, I, SH, $NH_2$, N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone, ε-caprolactone, $CH_2$=CH—C(=O)—O—, $CH_2$=CH—C(=O)—NH—, $CH_2$=CH—C(=O)—S—;

G is independently selected from H, F, Cl, Br, I, OH, SH, $NH_2$, N=C=O, N=C=S, COOH, COSH, C(=S)SH, OCOOH, OCOSH, OC(=S)OH, SC(=O)SH, SC(=S)SH, N(C=O)$NH_2$, N(C=NH)$NH_2$, N(C=S)$NH_2$, δ-valerolactone, ε-caprolactone, $CH_2$=CH—C(=O)—O—, $CH_2$=CH—C(=O)—NH—, $CH_2$=CH—C(=O)—S—; or absent B and F are selected independently from —$(CH_2)_x$—, where x is an integer from 0 to 20;

C is CH or N;

D is selected from —C(=O)$(CH_2)_x$C(=O)—, —C(=O)—, and —$(CH_2)_x$—, where x is an integer from 1 to 20;

E is O or N;

X is O, S, or N;

I is H or —$(CH_2)_x CH_3$, where x is an integer from 0 to 20;

n is an integer from 1 to 5; and

R is selected from the group consisting of hydrogen, C1-C20 alkyl, C6-C12 aryl, cyclic alkyl group (e.g., isobornyl, cyclohexyl, cyclopentyl), and fluoroalkyl (e.g., perfluorobutyl, perfluoroethyl).

The preparation of a representative ectoine monomer useful for making the polymers and copolymers of the invention is described in Example 11.

Ectoine polymers and copolymers. In other aspects, the invention provides ectoine polymers prepared from ectoine monomers and ectoine precursors, such as described herein, and that include ectoine or ectoine precursor repeating units.

The ectoine polymers and copolymers of the invention include polymers and copolymers prepared from monomers of formulae (VIIIA) and (VIIIB). Polymers can be formed by polymerization of (a) a monomer of formula (VIIIA) or (b) a monomer of formula (VIIIB). Copolymers can be prepared by copolymerization of (a) a monomer of formula (VIIIA) and a second comonomer that is suitable for copolymerization with a monomer of formula (VIIIA), (b) a monomer of formula (VIIIB) and a second comonomer that is suitable for copolymerization with a monomer of formula (VIIIB), and (c) a monomer of formula (VIIIA) and a monomer of formula (VIIIB) that is suitable for copolymerization with a monomer of formula (VIIIA).

Representative ectoine polymers and ectoine precursor polymers have repeating units of formulae (IxA) and (IxB), respectively:

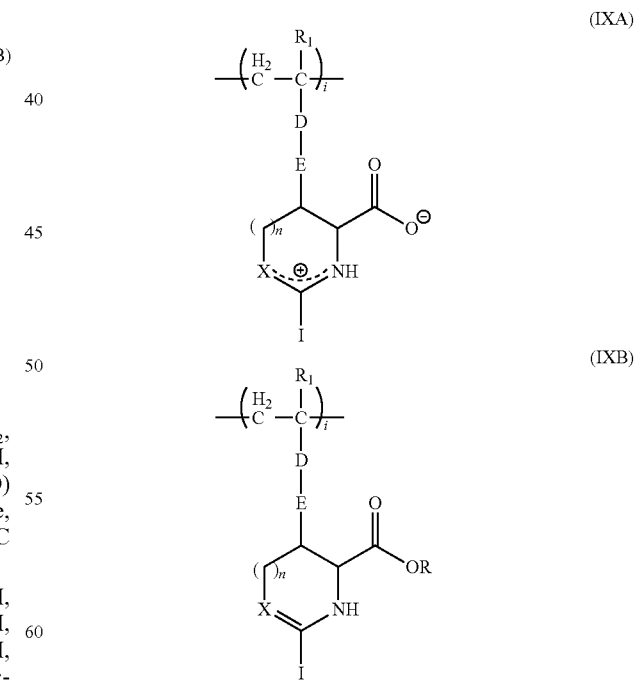

wherein

D is selected from —C(=O)$(CH_2)_x$C(=O)—, —C(=O)—, —$(CH_2)_x$—, where x is an integer from 1 to 20;

E is O or N;

X is O, S, or N;

I is H or —$(CH_2)_xCH_3$, where x is an integer from 0 to 20;

i is an integer from 2 to about 10,000;

n is an integer from 1 to 5;

$R_1$ is selected from H, $C_1$-$C_6$ alkyl, CN, and $NO_2$; and

R is selected from the group consisting of hydrogen, C1-C20 alkyl, C6-C12 aryl, cyclic alkyl group (e.g., isobornyl, cyclohexyl, cyclopentyl), fluoroalkyl (e.g., perfluorobutyl, perfluoroethyl).

In certain embodiments, the ectoine/ectoine precursor polymer or copolymer is a crosslinked ectoine/ectoine precursor polymer or copolymer. In certain embodiments, the crosslinked ectoine/ectoine precursor polymer or copolymer is prepared by copolymerization of the ectoine monomer or ectoine precursor monomer with ectoine crosslinking agent or an ectoine precursor crosslinking agent. Representative ectoine crosslinking agents and ectoine precursor crosslinking agents have formulae (XA) and (XB), respectively:

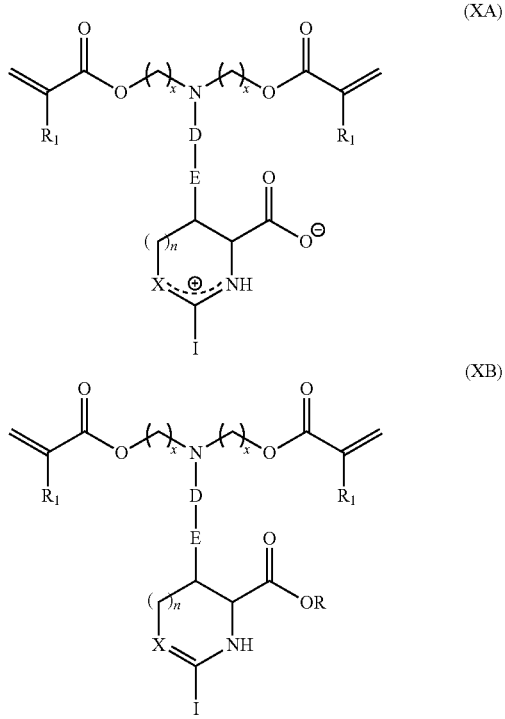

wherein $R_1$ is independently selected from H, C1-C5 alkyl, and CN;

x at each occurrence is independently selected from an integer from 1 to 5;

D is selected from —C(=O)$(CH_2)_x$C(=O)—, —C(=O)—, and —$(CH_2)_x$—, where x is an integer from 1 to 20;

E is O or N;

X is O, S, or N;

I is H or $(CH_2)_x$ $CH_3$, where x is an integer from 0 to 20;

n is an integer from 1 to 5;

R is selected from the group consisting of hydrogen, C1-C20 alkyl, C6-C12 aryl, cyclic alkyl group (e.g., isobornyl, cyclohexyl, cyclopentyl), and fluoroalkyl (e.g., perfluorobutyl, perfluoroethyl).

Ectoine Polymeric Surface Coatings, Bulk Materials, and Stand-Alone Materials

In other aspects, the present invention provides ectoine polymeric surface coatings, bulk materials, and stand-alone materials. In certain embodiments, the ectoine polymeric surface coatings, bulk materials, and stand-alone materials are prepared from ectoine monomers and polymers and copolymers prepared from ectoine monomers.

Ectoine polymers can be attached to surfaces (e.g., medical devices, sensors, membranes, ships and marine structures) via "graft-from" or "graft-to" methods to render the surfaces nonfouling. Ectoine polymers can be also blended with or into bulk materials (e.g., silicone). Surface coating can be on flat or nano/micro-particle surfaces. Ectoine polymers can also be prepared into stand-alone low-fouling and high-strength materials and devices for medical and marine applications via (i) unique backbones such as silicone, fluorinated, urethane, imide, amide and (ii) strong interactions such as multiple hydrogen bonds, and (iii) interpenetrating networks.

Ectoine Polymeric Surface Coatings.

The present invention provides ectoine polymeric surface coatings. In certain embodiments, the surface coating comprises an ectoine polymer (oligomer) or ectoine copolymer of the invention as described herein (e.g., a polymer of formulae (IXA) or (IXB). In certain embodiments, the coatings are prepared by a polymerizing or copolymerization process using a monomer of the invention as described herein (e.g., a monomer of formula (VIIIA) or (VIIIB)).

The surfaces coated with the ectoine polymers and copolymers have nonfouling properties. Nonfouling properties of the surfaces can be evaluated by fibrinogen adsorption and cell adhesion. In certain embodiments, surfaces of the invention have fibrinogen adsorption less than about 200 ng/cm². In other embodiments, surfaces of the invention have fibrinogen adsorption less than about 100 ng/cm². In further embodiments, surfaces of the invention have fibrinogen adsorption less than about 50 ng/cm². In other embodiments, surfaces of the invention have fibrinogen adsorption less than about 30 ng/cm². In further embodiments, surfaces of the invention have fibrinogen adsorption less than about 20 ng/cm². In other embodiments, surfaces of the invention have fibrinogen adsorption less than about 10 ng/cm². In certain embodiments, surfaces of the invention have fibrinogen adsorption less than about 5 ng/cm².

In certain embodiments, the surfaces are coated with an ectoine polymer or copolymer prepared from one or more ectoine monomers selected from the polymerizable groups comprising of, but not limited to ectoine acrylates, ectoine acrylamides, ectoine methacrylates, ectoine methacrylamides, ectoine vinyl compounds, ectoine epoxides and mixtures thereof. Representative ectoine monomers include those described herein, including ectoine monomers of formula (VIIIA) and formula (VIIIB).

In certain embodiments, the ectoine polymer or copolymer is a random, a multiblock, or a hyperbranched copolymer comprising a poly(ectoine). In other embodiments, the ectoine polymer or copolymer is an interpenetrating ectoine polymer network.

In certain embodiments, the ectoine polymer or copolymer is has surface adhesive groups (e.g., DOPA, thiol, silane, click chemistry, hydrophobic, hydrophilic, and charged groups).

The surfaces coated with the ectoine polymers and copolymers can be prepared by attaching the ectoine polymer or copolymers to a substrate surface via covalent interactions, physically hydrophobic-hydrophobic, charge-charge, and hydrogel-bonding interactions, or their combinations of chemical and physical interactions.

The surface coated with the ectoine polymers or copolymers can be prepared by grafting the ectoine polymers from the substrate surface ("grafted from") (e.g., preparing the polymeric surface by forming the polymer or copolymer by polymerizing suitable monomers in the presence of the substrate) or can be prepared by grafting the N-oxide polymers to the substrate surface ("grafted to") (e.g., preparing the polymeric surface by coupling the pre-formed polymer or copolymer to the substrate).

In certain embodiments, the ectoine polymers and copolymers are grafted from the substrate by polymerization methods, such as atom-transfer radical-polymerization (ATRP), reversible addition-fragmentation chain-transfer polymerization (RAFT), or photoinferter polymerization.

In certain embodiments, the ectoine polymers and copolymers are grafted to the substrate by conjugation methods, such as click chemistry, DOPA conjugation chemistry, or self-assembled monolayer (SAM) via thiol or silane.

The ectoine polymeric surface coatings can be applied to a variety of substrates (e.g., substrate surfaces). In certain embodiments, the surface is all or part of biomedical device. Representative biomedical devices include catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

In certain embodiments, the device is a contact lens.

In certain embodiments, the surface is all or part of a particle. Representative particles include metal, metal oxide, ceramic, synthetic polymer, natural polymer, silicon dioxide, crystal, and semiconductor material particles. In certain embodiments, the particle is a biomolecule, such as a protein (e.g., an enzyme) or a nucleic acid (e.g., a DNA or a RNA). In other embodiments, the particle is a cell.

In certain embodiments, the surface is all or part of a membrane or a bio-separation membrane. Representative membranes include membranes used for protein purification, wastewater treatment, bioreactors, desalination of sea water, and water/oil purification.

In certain embodiments, the device is a marine device. All or part of the surface of the marine device can be coated with the polymeric ectoine coating. Representative marine devices include marine products, such as marine vessel hulls, marine structures, bridges, propellers, heat exchangers, periscopes, sensors, fish nets, cables, tubes/pipes, containers, membranes, and oil booms.

In certain embodiments, the surface is on or forming all of a drug delivery vehicle, such as a gene delivery vehicle, an RNA delivery vehicle, or a protein delivery vehicle.

In certain embodiments, the surface is on or forming all or part of an implantable or subcutaneous sensor.

In certain embodiments, the surface is on or forming all or part of a tissue scaffold.

Ectoine Polymeric Bulk Materials.

The present invention provides ectoine polymeric bulk materials. In certain embodiments, the bulk materials comprises an ectoine polymer (oligomer) or ectoine copolymer of the invention as described herein (e.g., a polymer of formulae (IXA) or (IXB). In certain embodiments, the materials are prepared by a polymerizing or copolymerization process using a monomer of the invention as described herein (e.g., a monomer of formula (VIIIA) or (VIIIB)).

In certain embodiments, the bulk material is obtained by blending of one or more ectoine polymers or copolymers with one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

In other embodiments, the bulk material comprises an interpenetrating ectoine polymer network and one or more other polymers, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers.

Ectoine Polymeric Standalone Materials.

The present invention provides ectoine polymeric standalone materials. In certain embodiments, the materials comprise an ectoine polymer (oligomer) or ectoine copolymer of the invention as described herein (e.g., a polymer of formulae (IXA) or (IXB)). In certain embodiments, the materials are prepared by a polymerizing or copolymerization process using a monomer of the invention as described herein (e.g., a monomer of formula (VIIIA) or (VIIIB)).

In certain embodiments, the ectoine polymeric standalone materials are nonfouling materials and have high mechanical strength. In certain of these embodiments, the standalone material is a nonfouling material having protein adsorption less than about 30, less than about 50, or less than about 100 ng/cm$^2$, having tensile/compressive strengths greater than about, 0.2, greater than about 0.5, or greater than about 1.0 MPa.

In certain embodiments, the ectoine polymeric standalone material is an ectoine polymer network that is reinforced by introducing (a) dipole-dipole interactions such as cyano groups (C≡N) and (b) hydrogen donors/acceptors such as amide group (—(NH)—(C=O)—), multiple amide groups ((—(NH)—(C=O)—)$_n$ (n=1-5)), urethane group (—(NH)—(C=O)—O—), multiple urethane groups ((—(NH)—(C=O)—O—)$_n$ (n=1-5)), urea group (—(NH)—(C=O)—(NH)—), multiple urea groups ((—(NH)—(C=O)—(NH)—)$_n$ (n=1-5)), and their combinations. These groups can be derived from ectoine monomers and ectoine (random- or block-) copolymers.

The ectoine polymer networks can be reinforced with backbones in an ectoine monomer or an ectoine polymer, such as polyacrylate, polymethacrylate, polyacrylamide, polymethacrylamide, polyamide, polydimethylsiloxane, polyethylene, polypropylene, polystyrene, polytetrafluoroethylene, polyisobutene, polyesters, polycarbonates, polyurethanes, polyureas, polysulfides, polysulfones, polyimides, polyepoxies, polyanhydrides, polyethers, and other condensation/addition polymers. In certain embodiments, the ectoine polymer network is reinforced by any combination of the above.

In certain embodiments, the ectoine polymer can be form copolymers with other polymers or composites, such as polyesters, polycarbonates, polyurethanes, polyureas, polysulfides, polysulfones, polyimides, polyepoxies, aromatic polyesters, cellulosics, fluoropolymers, polyacrylics, polyamides, polyanhydrides, polyethers, vinyl polymers, phenolics, elastomers, and other addition polymers. Fiber, clays, nanotubes and other inorganic objects can be added to increase mechanical properties of these materials.

The ectoine standalone materials of the invention can be formed into an object by a variety of methods, such as injection molding, blow molding, extrusion molding, calendaring molding, flow casting, compression molding, prevarication molding, and 3D printing.

The ectoine standalone materials of the invention can be used in biomedical/biotechnological, consumer product, engineering/marine, therapeutics/diagnostics applications such as catheters, ear drainage tubes, feeding tubes, glaucoma drainage tubes, hydrocephalous shunt, keratoprosthesis, nerve guidance tubes, tissue adhesive, x-ray guide, an artificial joint, artificial heart valve, artificial blood vessel, pacemaker, left ventricular assist device (LVAD), artery graft, vascular grafts, stent, intravascular stent, cardiac valves, joint replacements, blood vessel prostheses, skin repair devices, cochlear replacements, contact lenses, artificial ligaments and tendons, dental implants and tissue scaffolds for regenerative tissue engineering, drug delivery, gene delivery, RNA delivery, protein delivery, marine and engineering devices/objects (e.g., membranes, tubes, pipes, containers, or plates).

In certain embodiments, the standalone materials can be used in marine products such as marine vessel hulls, marine structures, bridges, propellers, heat exchangers, periscopes, sensors, fish nets, cables, tubes/pipes, containers, membranes, and oil booms.

In certain embodiments, the standalone materials can be conjugated to a biomaterial. Representative biomaterials include nucleic acids (e.g., a gene, DNA, RNA), proteins (e.g., enzymes, antibody or functional fragment thereof), peptides, lipids, cells or microorganisms, solid nanoparticles (iron oxide, silica, quantum dot or gold nanoparticles), or used for protection against dehydration on skin by surfactants.

Ectoine Polymeric Hydrogels

The present invention provides ectoine polymeric hydrogels. In certain embodiments, the hydrogel comprises a crosslinked ectoine polymer (oligomer) or ectoine copolymer of the invention as described herein (e.g., a polymer of formulae (IXA) or (IXB)). In certain embodiments, the hydrogels are prepared by a polymerizing or copolymerization process using a monomer of the invention as described herein (e.g., a monomer of formula (VIIIA) or (VIIIB)).

Ectoine polymeric hydrogels can be created from N-oxide monomers and various crosslinkers, including degradable or non-degradable ectoine crosslinkers. Ectoine star polymers can be prepared by forming hydrogels (e.g., via click chemistry). These hydrogels can be in the form of bulk hydrogels or pellet hydrogels. These hydrogels can be used as implantable materials and devices to reduce capsule formation and as media to protect, expand, preserve and differentiate various cells (e.g., stem cells, immune cells, islets, platelets and cardiomyocytes) in controlled manners. Pellet and star hydrogels can be injectable along with biologics (e.g., various cells and tumor for tumor vaccine).

In certain embodiments, the ectoine hydrogel is a crosslinked hydrogel prepared from one or more ectoine monomers (e.g., a monomer of formula (VIIIA) or (VIIIB)) using one or more crosslinkers.

In certain of these embodiments, the crosslinker is an ectoine crosslinker (e.g., a crosslinker of formula (XA) or (XB)).

In other of these embodiments, the crosslinker is a multifunctional zwitterionic crosslinker that includes carboxybetaine, sulfobetaine, or phosphobetaine moieties.

In further of these embodiments, the crosslinker is a multifunctional crosslinker, such as N,N'-methylenebisacrylamide (MBAA), polyethylene glycol (PEG) diacrylate or diacrylamide, or PEG dimethacrylate or dimethacrylamide.

In certain embodiments, the hydrogel is prepared using a bifunctional ectoine crosslinker. In other embodiments, the hydrogel is prepared using a degradable or non-degradable crosslinker. In further embodiments, the hydrogel is prepared using a degradable, zwitterionic disulfide crosslinker. In other embodiments, hydrogel is prepared using peptide based crosslinker that can be degraded by enzymes or suitable agents.

The ectoine hydrogels of invention can be prepared by free radical mediated polymerization techniques, such as thermos-, photo-, or redox.

The ectoine hydrogels of invention can be used for biosensors and biomedical devices, vascular grafts, intravascular stents, cardiac valves, joint replacements, cell preservation/expansion/differentiation, drug delivery platforms, ship hulls, marine structures/equipment, and other materials and devices that come into contact with physiological environments.

In certain embodiments, the ectoine hydrogel is a star hydrogel. Star hydrogels can be prepared from a polymer having a core and a plurality of ectoine or other zwitterionic branches covalently coupled to the core. Representative cores include one of a small molecule, oligomer, or polymer of or star shapes with three, four, five or more branches.

In certain embodiments, the hydrogel is crosslinked by a degradable crosslinker that can be selectively degraded (i.e., under specific conditions). The degradable crosslinker can be selected from peptide crosslinkers, polysacharride crosslinkes, anhydride crosslinkers, dissulfide crosslinkers, and polyester crosslinkers. For certain of these embodiments, the hydrogel can be hydrolyzed or digested by enzymes.

The preparation of a representative ectoine polymer hydrogel is described in Example 12. Fibrinogen and cell adsorption for representative ectoine polymer hydrogels is described in Example 13.

Other Ectoine Polymer Compositions

In another aspect, the invention provides nano- and microparticles comprising the ectoine polymers and copolymers of the invention.

In a further aspect, the invention provides ectoine polymer and copolymer conjugates.

In yet another aspect, the invention provides ectoine polymer nanogels and nanocages.

In certain embodiments, these compositions comprise a crosslinked ectoine polymer (oligomer) or ectoine copolymer of the invention as described herein (e.g., a polymer of formulae (IXA) or (IXB)). In certain embodiments, these compositions are prepared by a polymerizing or copolymerization process using a monomer of the invention as described herein (e.g., a monomer of formula (VIIIA) or (VIIIB)).

The nano- and microparticles, ectoine polymer and copolymer conjugates, and ectoine polymer and copolymer conjugates can be prepared as described herein for their counterpart N-oxide compositions and can be used as described herein for their counterpart N-oxide compositions.

As used herein, the term "about" refers to +10 percent of the specified value.

The following examples are provided for the purpose of illustrating, not limiting, the invention.

EXAMPLES

Example 1

Synthesis and Purification of a Representative Polymerizable N-Oxide Monomer

In this example, the synthesis and purification of a representative polymerizable N-oxide monomer, DMAPA N-oxide, are described.

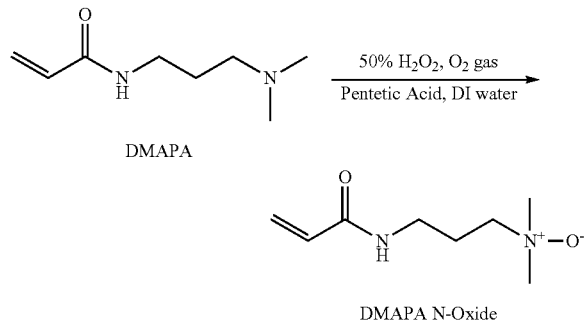

800 mg of diethylenetriaminepentaacetic acid was added to 30 mL of DI water. Then hydrogen peroxide (50% solution, 2.87 g) was added and reaction contents were heated followed by purging of the oxygen gas. Dimethylaminopropylacrylamide (DMAPA) (14.4 g) in 10 mL DI water was then added. After completion of reaction, the reaction contents were cooled. The aqueous solution was then slowly added to acetone and the resulting thick viscous liquid settling at the bottom was separated by decantation of the supernatant. This liquid was further washed with diethyl ether and the resulting desired N-oxide monomer was obtained as thick viscous liquid. NMR and mass spectrometry analysis confirmed the identity of the DMAPA N-oxide monomer.

$^1$H NMR (500 MHz, D$_2$O): δ 6.07-5.93 (m, 2H), 5.55 (d, J=9.9 Hz, 1H), 3.12 (m, 4H), 3.01 (s, 6H), 1.90-1.74 (m, 2H).

LRMS (ESI): m/z: 173 [M+H]$^+$.

Example 2

Nonfouling Properties of a Representative N-Oxide Polymer Surface

In this example, nonfouling properties of a representative N-oxide polymer surface, a DMAPA N-oxide polymer brush, are described.

SI-ATRP technology was applied to graft TMAO polymer brushes onto a glass substrate coated with gold surface. A self-assembly monomer layer (SAM) was formed by soaking clean gold coated glass substrate in ω-mercaptoundecyl bromoisobutyrate solution (0.2 mmol/L in ethanol) for overnight. The initiator coated substrates, together with copper(I) bromide (14.35 mg, 0.1 mmol) were then placed into a Schlenk tube and deoxygenated via pump-vacuum for ten cycles. TMAO monomer (1.72 g, 10 mmol), prepared as described in Example 1, Me$_6$TREN (23 mg, 0.1 mmol), methanol (3.6 mL) and water (0.4 mL) were added into Schlenk tube and deoxygenated via the same method. After fully deoxygenation, the mixed aqueous solution of TMAO monomer and Me$_6$TREN were transferred to the tube which held the substrate and copper bromide. The reaction mixture was placed at ambient temperature for overnight. The substrate was then taken out from mixture and washed with ethanol and water, respectively, for three times and air-dried before being used as SPR sample. The thickness of the coated surface was later characterized by ellipsometry.

To implement SPR, a bare glass substrate was firstly loaded onto a SPR sensor (Institute of Photonics and Electronics, Prague, Czech Republic) for primary cleaning. All flowing pipes were washed by flowing RBS (soap solution), aqueous hydrochloric acid, DI water and PBS buffer. The glass substrate was then replaced with TMAO-coated substrate for characterization. PBS was allowed to flow all testing pipes until there is no bubble on the surface of TMAO-coated substrate. The instrument and software were set up following the SPR instructions. The characterization started with 10 minutes flow of PBS buffer, then followed by 10 minutes flow of 100% human serum and 10 minutes of PBS buffer. The instrument was cleaned by flowing RBS, DI water and air after experiment.

One SPR sensor curve for DMAPA N-oxide coatings is shown in FIG. 1 (10 nm in film thickness and 2.2 ng/cm$^2$ adsorbed proteins). Two other two experiments were performed to adjust film thickness to 20 and 24 nm and each achieved ultra-low nonfouling properties (<5 ng/cm$^2$).

Example 3

Preparation of a Representative N-Oxide Polymer Hydrogel

In this example, the preparation of a representative N-oxide polymer hydrogel, DMAPA N-oxide polymer hydrogel, is described.

A DMAPA N-oxide hydrogel was fabricated by bulk photo-polymerization with a hydrogel aqueous solution containing 33 wt % of DMAPA N-oxide monomer (prepared as described above in Example 1), 1 wt % (relative to monomer) of crosslinker N,N'-methylenebis(acrylamide), and 1 wt % (relative to monomer) of photo-initiator 2-hydroxy-2-methylpropiophenone. The hydrogel aqueous solution was placed between two glass slides separated by 0.5 mm-thick polytetrafluoroethylene spacers, and was then photo-polymerized at room temperature for 30 mins. After polymerization, hydrogels were removed from the casts and soaked in phosphate buffered saline (PBS) for three days to remove unreacted chemicals and reach the fully hydrated hydrogel network. Phosphate buffered saline was refreshed every 12 hours.

Example 4

Protein Adsorption and Cell Adhesion to a Representative N-Oxide Polymer Hydrogel In this example, protein adsorption and cell adhesion to a representative N-oxide polymer hydrogel, DMAPA N-oxide polymer hydrogel, are described.

Protein Adsorption.

Fibrinogen is a blood protein known to easily adsorb onto various surfaces through non-specific interactions. The surface adsorption of fibrinogen on the DMAPA N-oxide polymer hydrogel was quantified by an enzyme-linked immunosorbent assay (ELISA) method. The ELISA method is described as below and the results are shown in FIG. 2A.

Biopsy punches were used to punch the hydrated DMAPA N-oxide polymer hydrogel sheet into 5 mm-diameter disks.

Hydrogel disks were placed into wells of a 24 well-plate and incubated with 1 mL of 1 mg/mL fibrinogen in PBS buffer for 1 hour, followed by 5 washes with pure PBS buffer. Hydrogel disks were then transferred to new wells and incubated with 1 mL of horseradish peroxidase (HRP) conjugated anti-fibrinogen (1 µg/mL) in PBS buffer for 1 hour. All hydrogel disks were then transferred to new wells after 5 washes with pure PBS buffer. Next, 1 mL of 1 mg/mL o-phenylenediamine (OPD), 0.1 M citrate phosphate pH 5.0 solution, containing 0.03% hydrogen peroxide was added. After 15 min incubation, the enzymatic reaction was stopped by adding an equal volume of 1 N HCl. Absorbance value at 492 nm was recorded by a plate reader (Cytation 3, BioTek, Winooski, Vt.), and was normalized to that of polypropylene (PP) sample. Average data were acquired from three specimens.

Figure 2A:
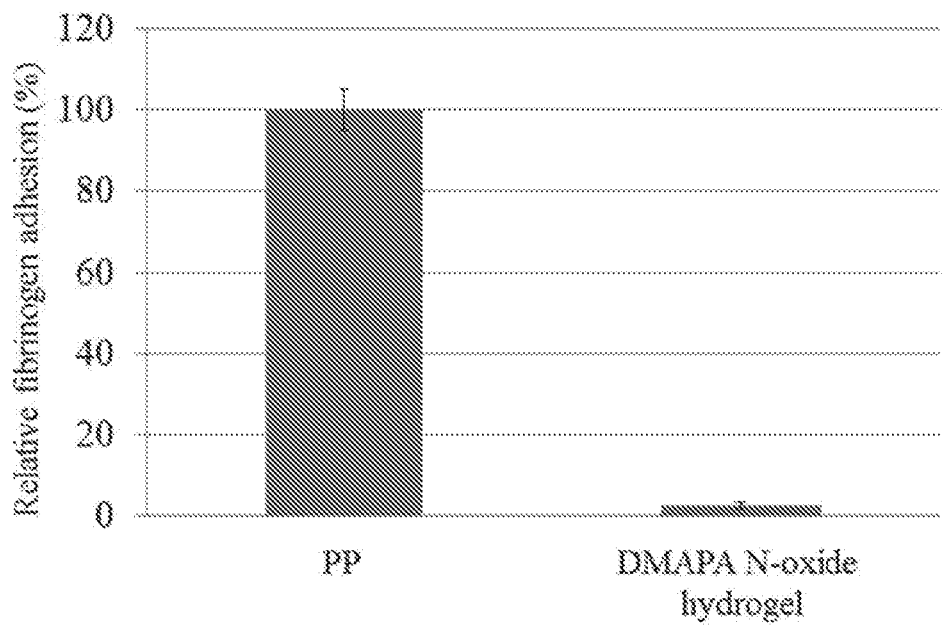
FIG. 2A compares relative fibrinogen adhesion of a representative N-oxide polymer hydrogel, DMAPA N-oxide polymer hydrogel, relative to polypropylene (PP) using an ELISA method.

As shown in FIG. 2A, the DMAPA N-oxide polymer hydrogel exhibited excellent nonfouling ability by decreasing 97.3% of fibrinogen adhesion with respect to that of polypropylene.

Cell Adhesion.

Figure 2B:
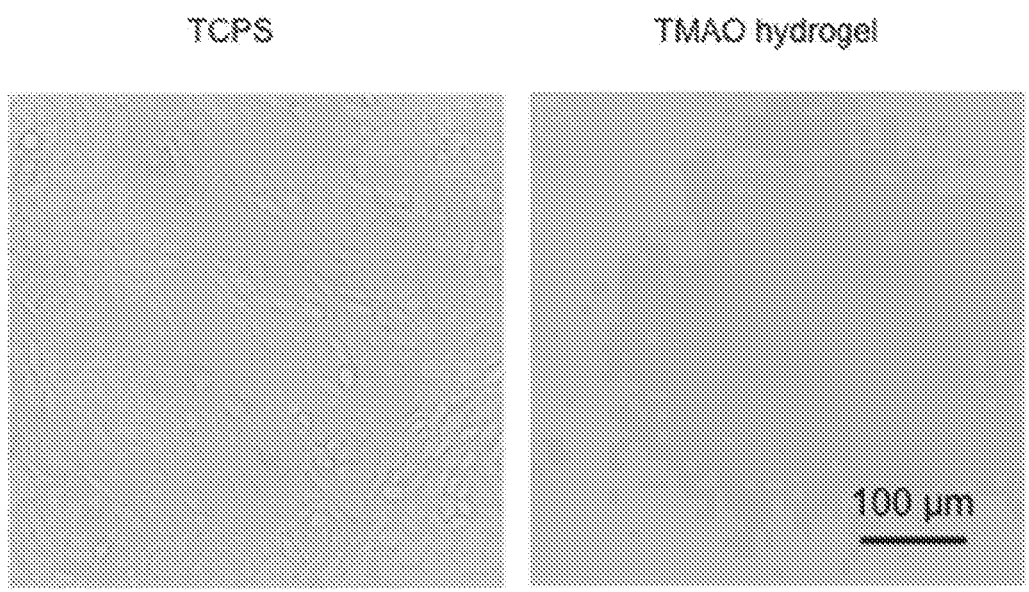
FIG. 2B compares images of cell adhesion on a representative N-oxide polymer hydrogel surface, DMAPA N-oxide polymer hydrogel surface (TMAO hydrogel), and a tissue culture polystyrene (TCPS) surface.

NIH3T3 mouse embryonic fibroblast cells were seeded into a 24-well tissue culture plate containing a piece of the DMAPA N-oxide polymer hydrogel (TMAO hydrogel) ($\Phi$=5 mm) at a concentration of $1.5 \times 10^5$ cells/ml in DMEM supplemented with 10% FBS at 37° C. in a humidified atmosphere containing 5.0% carbon dioxide. After 3 days of incubation, the medium was replaced. The morphologies of the cells on the tissue culture polystyrene (TCPS) surface and the TMAO hydrogel were observed using a Nikon Eclipse TE2000-U microscope. As shown in FIG. 2B, TMAO hydrogel effectively resists cell adhesion.

Example 5

Platelet Preservation Using a Representative N-Oxide Polymer Pellet Microgel

In this example, the use of a representative N-oxide polymer hydrogel, DMAPA N-oxide polymer pellet microgel, to store and preserve platelets for extended times is described. The results for platelet preservation using a DMAPA N-oxide polymer pellet microgel are shown in FIG. 3. Morphology score is defined as (% discs*4)+(% Spheres*2)+(% Dendrites*1)+(Balloon/Foreign Body Giants*0) where the maximum score is 400, but samples may vary when fresh platelets are taken usually around 380-400. Morphology scoring on platelets at Day 5 and Day 7 for the DMAPA N-oxide polymer pellet microgel was studied for effects of storage media on platelet encapsulation.

Example 6

Preparation of a Representative N-Oxide Polymer Protein Conjugate

In this example, the preparation of a representative N-oxide polymer (DMAPA N-oxide polymer) protein (uricase) conjugate is described.

Well-controlled Boc protected DMAPA N-oxide polymer was obtained via ATRP. ATRP initiator was synthesized by dissolving N-Boc-ethylenediamine (0.4806 g, 3 mmol) and triethylamine (0.334 g, 3.3 mmol) in 100 mL tetrahydrofuran. 2-Bromo-2-methylpropionyl bromide (0.7586 g, 3.3 mmol) was dissolved in 30 mL tetrahydrofuran and then added dropwise. The reaction was allowed to stir at 0° C. for overnight. The product tert-butyl N-[2-(2-bromo-2-methyl-propanamido)ethyl]carbamate (1) was then purified by chromatographic column. To carry out polymerization, 1 (30.7 mg, 0.1 mmol), DMAPA N-oxide monomer (1.72 g, 10 mmol) was placed into a Schlenk tube and deoxygenated via nitrogen-vacuum. Deoxygenated mix solvent (water and methanol) (2 mL) was added to dissolve all solids. The solution was then transferred via syringe to another Schlenk tube, contains tris[2-(dimethylamino)ethyl]amine (23 mg, 0.1 mmol), copper (I) bromide (14.3 mg, 0.1 mmol) and 2 mL mix solvent and was previously degassed and filled with nitrogen. The reaction mixture was allowed to stir at room temperature for overnight. The desired product, Boc-protected DMAPA N-oxide polymer was further purified via dialysis.

Figure 4A:
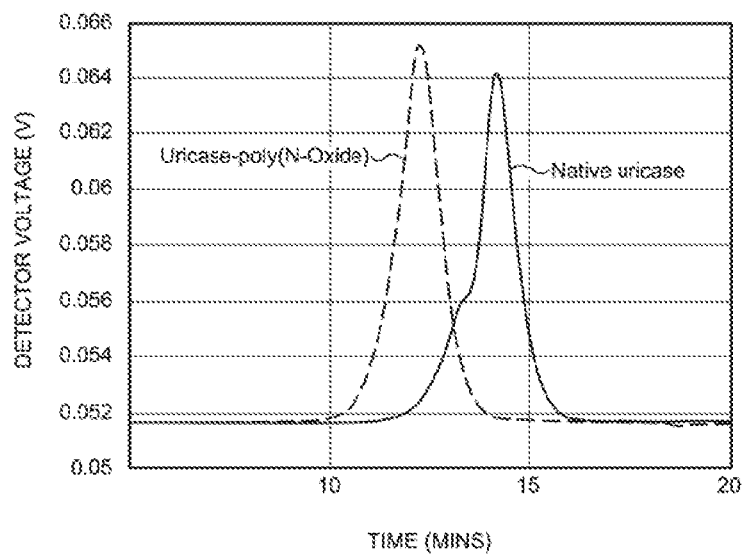
FIG. 4A compares gel permeation chromatographs for native uricase and poly(DMAPA N-oxide) conjugated uricase.
Figure 4B:
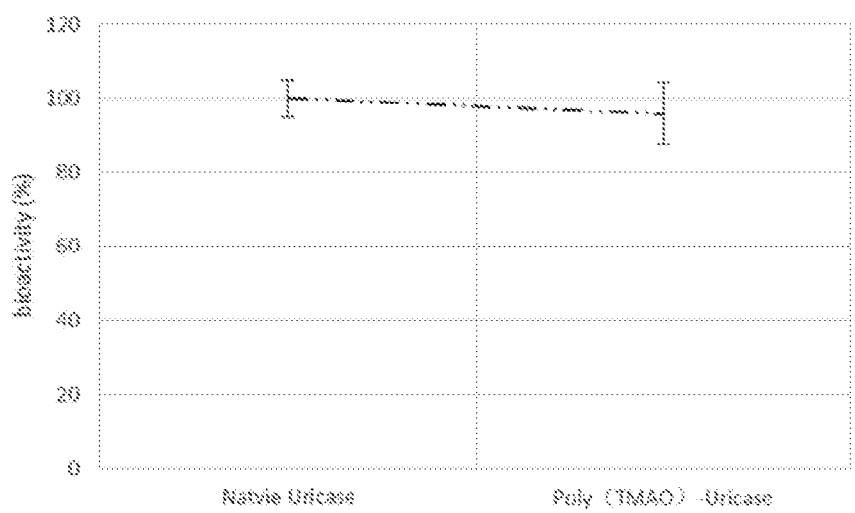
FIG. 4B compares relative bioactivity of uricase before and after N-oxide polymer conjugation.

500 mg Boc-protected DMAPA N-oxide polymer was dissolve in 5 mL trifluoroacetic acid (TFA) and stirred for 2 hours at room temperature to remove the Boc protecting group and obtain amine terminated DMAPA N-oxide polymer. The product was purified via dialysis. Then 150 mg of amine-terminated DMAPA N-oxide polymer together with 1.38 mg Traut's reagent were dissolved in 5 mL PBS buffer and stirred for two hours at room temperature to introduce thiol (—SH) reactive groups into DMAPA N-oxide polymer. Meanwhile, 3 mg uricase and 37.5 µL N-β-maleimidopropyloxysuccinimide ester (BMPS) solution (40 mg/ml in DMSO) were dissolved in 5 mL PBS, stirred for 1 hour at room temperature to modify protein with accessible double bond. Unreacted BMPS was removed by ultrafiltration (35K). Double bond modified uricase was then mixed with thiol-terminated DMAPA N-oxide polymer solution and reacted at 4° C. for overnight. The uricase conjugate was purified by ultrafiltration (100K) and characterized by GPC. FIG. 4A compares gel permeation chromatographs for native uricase and poly(DMAPA N-oxide) conjugated uricase. Amplex™ Red Uricase Assay Kit (Purchase from Thermo Fisher Scientific) was used to characterize the bioactivity changes of uricase after conjugation. Results show that uricase activity only dropped approximately 10% after conjugation (see FIG. 4B). This means N-oxide polymer conjugation can protect protein without scarifying protein activity. In vitro results show that N-oxide polymers work well for protein conjugation.

Example 7

Immunogenicity of a Representative N-Oxide Polymer Protein Conjugate

In this example, the immunogenicity of a representative N-oxide polymer protein conjugate, (poly(DMAPA N-oxide) uricase conjugate, is described.

To examine the immunogenic potential of a representative N-oxide polymer, DMAPA N-oxide polymer and keyhole limpet hemocyanin (KLH) conjugate was evaluated. KLH is a one of the most immunogenic proteins commonly used as the carrier to amplify the immunogenicity of grafted haptens. PEGylated KLH conjugates were prepared as the control. Briefly, KLH (1 mg/mL) and mPEG-NHS (10 kDa, 1 mg/mL) were mixed in 50 mM Hepes buffer (pH 8.5). The reaction was stirred at 4° C. overnight. Then the conjugates were concentrated and washed with PBS (pH 7.4) for five times using a 300 kDa molecular weight cutoff centrifugal filter. DMAPA N-oxide polymer-KLH conjugate and PEGylated KLH conjugate were subcutaneously (SC) injected into two cohorts of male C57BL/6J mice (five per group) respectively for four weeks (one dose per week). At the end of the fourth week (28th day), all the mice were sacrificed, and their blood collected through cardiac puncture were handled for direct ELISA test of anti-polymer antibodies (Abs). For ELISA test, the detection of anti-PEG antibody and anti-PCB antibody requires PEG-BSA conjugates and DMAPA N-oxide polymer-BSA conjugates as antigens. PEG-BSA conjugates were prepared following the same preparation protocol of PEG-KLH conjugates as described above. To prepare DMAPA N-oxide polymer-BSA conjugates, BSA was first modified with acryloyl group by adding 37 µL N-acryloxysuccinimide (NAS) dimethyl sulfoxide (DMSO) solution (20 mg/mL) into BSA solution (10 mg, dissolved in 5 mL 50 mM HEPES buffer (pH 8.5)). This reaction was stirred at 4° C. for 2 h. Then, PCB-BSA conjugates were formed via in situ radical polymerization by adding DMAPA N-oxide monomer (400 mg, dissolved in 5 mL HEPES buffer at pH 8.5) and initiators (20% (w/v) APS in deionized water (50 µL), and TEMED (30 µL)) into the former BSA solution. After 2 h stirring, the reaction mixture was concentrated and washed with PBS (pH 7.4) for five times using 300-kDa molecular weight cutoff centrifugal filters.

Figure 5:
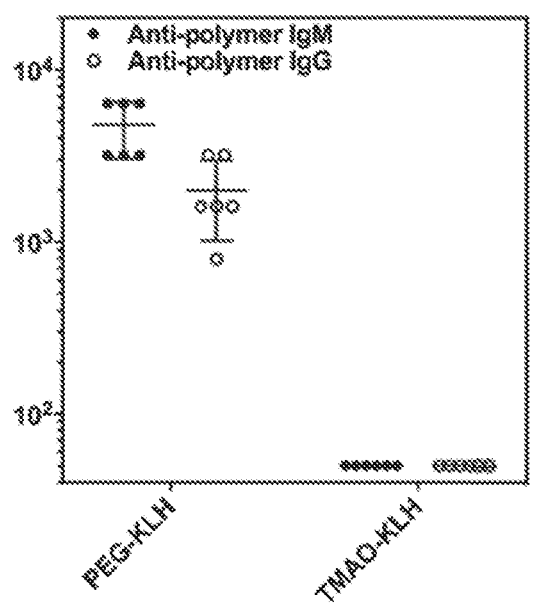
FIG. 5 compares ELISA method results for immunogenicity: Ab responses (anti-polymer IgM and anti-polymer IgG) towards PEG or representative N-oxide polymer (DMAPA N-oxide polymer) after four weekly subcutaneously administrations of PEG-KLH or DMAPA N-oxide polymer-KLH (TMAO-KLH) conjugates in mice.

As the first step of direct ELISA test, 100 µL antigen solutions (10 µg/mL of protein concentration) prepared in coating buffer (0.1 M sodium carbonate buffer, pH 10.5) were used to coat each well of 96-well plates. After overnight coating at 4° C. overnight, the plates were washed five times using PBS buffer (pH 7.4) to remove the antigen solutions and then filled with blocking buffer (1% BSA solution in 0.1 M Tris buffer, pH 8.0) for 1 hour incubation at room temperature, subsequent to which the blocking buffer was removed. All wells were then washed by PBS buffer for another five times. Subsequently, serial dilutions of rat sera in PBS buffer containing 1% BSA were added to the plates (100 µL/well) for 1 hour incubation at 37° C., subsequent to which the rat sera were removed and all wells were washed five times with PBS buffer. Next, goat anti-rat IgM or IgG (HRP-conjugated, Bethyl Laboratories) as the secondary antibody were added into each well for another 1 hour incubation at 37° C. Subsequently, all the wells were washed five times using PBS buffer before the addition of 100 µL/well HRP substrate 3,3',5,5'-tetramethylbenzidine (TMB; Bethyl Laboratories). The plates were shaken for 15 min, and 100 µL stop solution (0.2 M H$_2$SO$_4$) was added to each well. Absorbance at 450 (signal) and 570 nm (background) was recorded by a microplate reader. Mice sera naïve to the administration of KLH conjugate samples were used as the negative control for all ELISA detections. The results are shown in FIG. 5.

Example 8

Representative N-Oxide Polymer Nanocage for Protein Encapsulation

In this example, the preparation of a representative N-oxide polymer nanocage for protein encapsulation is described.

AOT (sodium bis(2-ethylhexyl) sulfosuccinate, 237 mg) and Brij 30 (poly(ethylene glycol) dodecyl ether, 459 mg) were added to a 20 mL glass vial to which a stir bar was added. The vial was sealed with a Teflon-lined septum cap and purged with dry nitrogen for 10 min. Nitrogen-deoxygenated hexane (10 mL) was then added to the vial under vigorous stirring. For the aqueous phase, protein (e.g., KLH, 2 mg) was dissolved in Hepes buffer (pH 8.5, 250 µL) to which DMAPA N-oxide monomer (200 mg) and N,N'-methylenebis(acrylamide) (20 mg) were added and dissolved. Dry nitrogen was bubbled through the monomer/ protein solution for 2 min, after which the aqueous phase was slowly added to the organic continuous phase dropwise. The vial was sonicated to form a stable microemulsion. A 20% (w/v) solution of ammonium persulfate (APS) in deionized water (10 ul) was then added to the emulsion. After 5 min, polymerization was initiated by the addition of tetramethylethylenediamine (TEMED, 6 uL) and maintained at 4° C. under rapid magnetic stirring. After the 2 hour reaction, the organic solvent was removed by rotary evaporator and the nanocage was precipitated and washed with THF for three times. The nanocage was re-suspended in PBS buffer and purified with 300 kDa molecular weight cutoff centrifugal filters to remove the free protein.

Figure 6A:
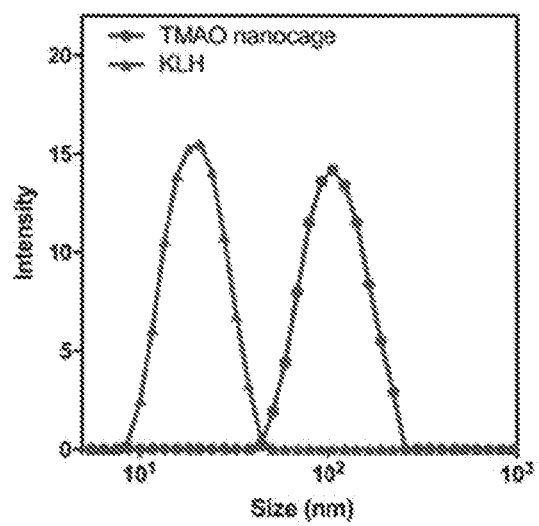
FIG. 6A compares size distribution of a representative N-oxide polymer nanocage, DMAPA N-oxide polymer nanocage (TMAO nanocage), encapsulating KLH and free KLH (KLH) as measured by dynamic light scattering.
Figure 6B:
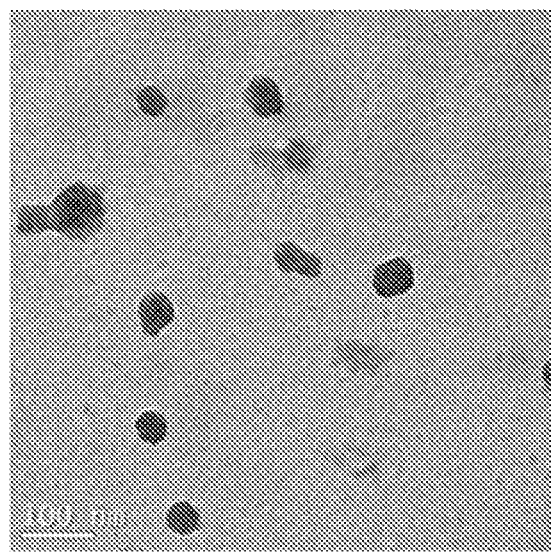
FIG. 6B is a tunneling electron microscopy (TEM) image of the representative N-oxide polymer nanocage of FIG. 6A.

FIG. 6A compares size distribution of DMAPA N-oxide polymer nanocage encapsulating KLH and free KLH as measured by dynamic light scattering. FIG. 6B is a tunneling electron microscopy (TEM) image of the DMAPA N-oxide nanocage.

Example 9

Protein-Stabilizing Effect of a Representative N-Oxide Polymer Protein Nanocage

In this example, the protein-stabilizing effect of a representative N-oxide polymer protein nanocage is described.

For thermal stability test, modified uricase samples in PBS buffer (pH 7.4) were incubated at a 60° C. in water bath for 5, 10, 20, 40, and 60 minutes, after which each sample was taken out and quenched in an ice bath for the assay of uricase activity.

Figure 7:
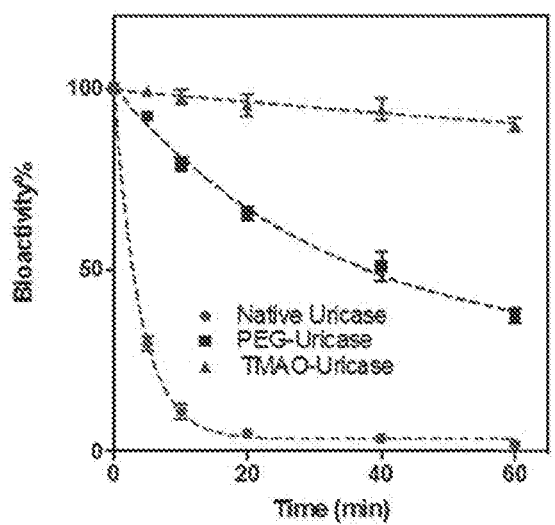
FIG. 7 compares thermal stabilities of native uricase, PEG-uricase, and a representative N-oxide polymer-nanocage-protected uricase (TMAO-uricase).

FIG. 7 compares thermal stabilities of native uricase, PEGylated uricase, and a representative N-oxide polymer-nanocage-protected uricase.

Example 10

Pharmacokinetics of Proteins with a Representative N-Oxide Protein Nanocage

In this example, the improvement of pharmacokinetics of representative proteins using a representative N-oxide protein nanocage is described.

The pharmacokinetics (PK) of native uricase, PEGylated uricase, and N-oxide polymer nanocage-protected uricase are compared in male C57BL/6J mice (five per group). Each protein sample was intravenously (IV) administered into the rat via orbital vein injection at the dose of 25 U/kg body weight. Blood samples were collected from the tail vein at 5 min, 2 h, 6 h, 24 h, and 48 h after the injection. The blood samples were put in heparinized vials and centrifuged, and the enzyme content in plasma was estimated by enzyme activity.

FIG. 8 compares blood circulation profiles of a representative N-oxide polymer nanocage-modified uricase, a PEGylated uricase, and native uricase.

Example 11

Synthesis of a Representative Ectoine Polymerizable Monomer

In this example, the synthesis of a representative ectoine polymerizable monomer, ectoine methacrylate monomer, is described.

Hydroxyectoine (2 gm, 12.6 mmol) was dissolved in 8 mL TFA with vigorous stirring at 0° C. After dissolution of starting material, trifluoromethane sulfonic acid (0.37 gm, 2.4 mmol) was added and reaction contents were stirred for 5 min. Then methacryloyl chloride (2.44 mL, 25.2 mmol) was added to the reaction mixture and stirred for 2 hours. After 2 hours, 30 mL diethyl ether was added slowly to reaction mixture at 0° C. to give the compound as white powder. The crude white solid was further crystallized with methanol: diethyl ether to give desired monomer.

A small amount of monomer was dissolved in water to check for its purity with analytical HPLC. The ectoine monomer obtained by this method had 72% purity with starting material hydroxyectoine as impurity. A small amount of this product was further purified by HPLC for NMR analysis.

$^1$H NMR (500 MHz, D$_2$O): δ 6.07 (s, 1H), 5.7 (s, 1H), 5.59 (d, J=2.4 Hz, 1H), 4.47 (s, 1H), 3.63 (d, J=15.3 Hz, 1H), 3.46 (d, J=14.95 Hz, 1H), 2.3 (s, 3H), 1.84 (s, 3H).

Example 12

Preparation of Representative Ectoine Polymer Hydrogels

In this example, the preparation of representative ectoine polymer hydrogels, poly(ectoine) hydrogels, is described.

Poly(ectoine) hydrogels were made by thermal polymerization of an aqueous solution composed of ectoine monomer with weight equal to that of water, X wt % (relative to the weight of ectoine monomer) crosslinker N',N'-methylenebis(acrylamide) and 1 wt % (relative to the weight of ectoine monomer) thermal initiator 2,2'-azobis(2-methylpropionamidine) dihydrochloride. Poly(ectoine) hydrogels with three different crosslinker amounts (X=0.5, 1, 1.5) were prepared. The ectoine monomer solutions were polymerized between glass microscope slides separated by 0.8 mm-thick polytetrafluoroethylene spacers at 35° C. for 2 hours followed by 50 OC for 40 hours. The formed poly(ectoine) hydrogels were soaked into PBS (0.01 M phosphate buffer, 0.0027 M potassium chloride and 0.137 M sodium chloride, pH 7.4) to hydrate. The PBS was changed daily for five days to remove unreacted chemicals and let the poly(ectoine) hydrogels reach the swelling equilibrium. Afterward, the poly(ectoine) hydrogels were cut into rectangular shape or by biopsy punches into disks with diameter and thickness in 5 mm and about 1.5 mm respectively, before further tests.

Hydration Properties of Representative Poly(Ectoine) Hydrogels.

Figure 9:
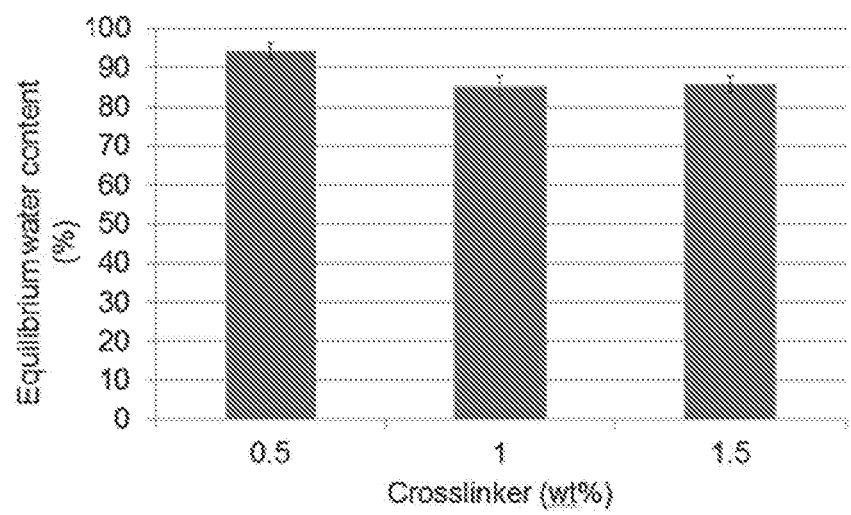
FIG. 9 compares equilibrium water content of representative poly(ectoine) hydrogels prepared with different crosslinker amounts (0.5, 1, 1.5 wt %).

The relative equilibrium water content (EWC) of the poly(ectoine) hydrogels is shown in FIG. 9, where the EWC is calculated based on the mass of dry and swollen hydrogel. An increase in crosslinker content resulted in a decrease of hydration. For the poly(ectoine) hydrogels with crosslinkers at the range of 0.5 to 1.5 wt %, the EWC decreases from 94% to 85%.

Mechanical Properties of Representative Poly(Ectoine) Hydrogels.

Figure 10A:
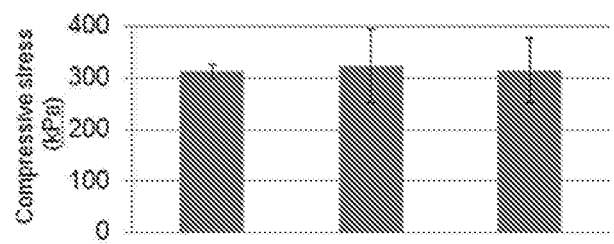
FIGS. 10A-10C compare compressive stress, compressive strain at fracture point, and compressive modulus of representative poly(ectoine) hydrogels prepared with different crosslinker amounts (0.5, 1, 1.5 wt %), respectively.
Figure 10B:
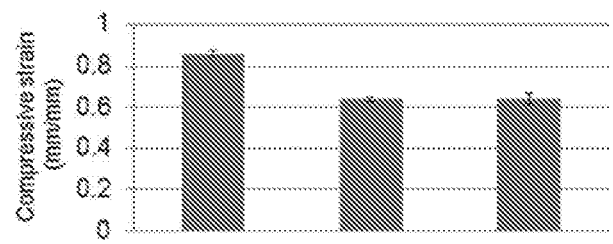
Figure 10C:
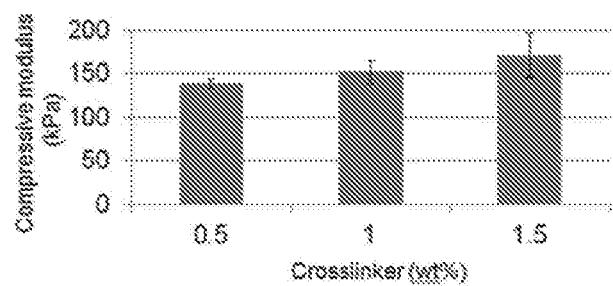

The mechanical properties of the representative poly (ectoine) hydrogels were directly measured by compression testing. The compressive stress, compressive strain at break, and compressive modulus as a function of crosslinker amount are compared in FIGS. 10A, 10B, and 10C, respectively (ASTM D6641: Standard Test Method for Compressive Properties of Polymer Matrix Composite Materials Using a Combined Loading Compression (CLC) Test Fixture).

Example 13

Fibrinogen and Cell Adsorption for Representative Poly(Ectoine) Hydrogels

In this example, fibrinogen and cell adsorption for the representative poly(ectoine) hydrogels is described. Fibrinogen adhesion of poly(ectoine) hydrogels by enzyme-linked immunosorbent assay (ELISA) test was determined.

Figure 11:
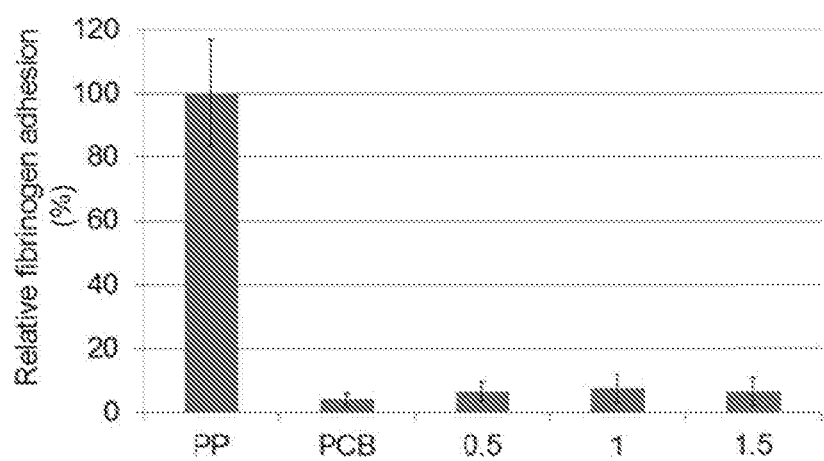
FIG. 11 compares relative fibrinogen adhesion of representative poly(ectoine) hydrogels prepared with different crosslinker amounts (0.5, 1, 1.5 wt %) as measured by ELISA. Polypropylene (PP) sheet and a representative poly(carboxybetaine) (PCB) hydrogel were used as positive and negative controls, respectively. Data was normalized to PP.

The surface adsorption of fibrinogen was quantified by an enzyme-linked immunosorbent assay (ELISA) method, and the results are shown in FIG. 11. Each of the three tested poly(ectoine) hydrogels prepared with crosslinker amounts of 0.5, 1, and 1.5 wt %, respectively, exhibited excellent nonfouling ability by decreasing 97.0%, 95.8%, and 95.6% of fibrinogen adsorption, respectively, compared to that of polypropylene (PP) as the positive control, and was comparable to results obtained for a representative poly(carboxybetaine) hydrogel (PCB) (fabricated with 1% MBAA crosslinker and used after full swell) as a negative control.

Figure 12:
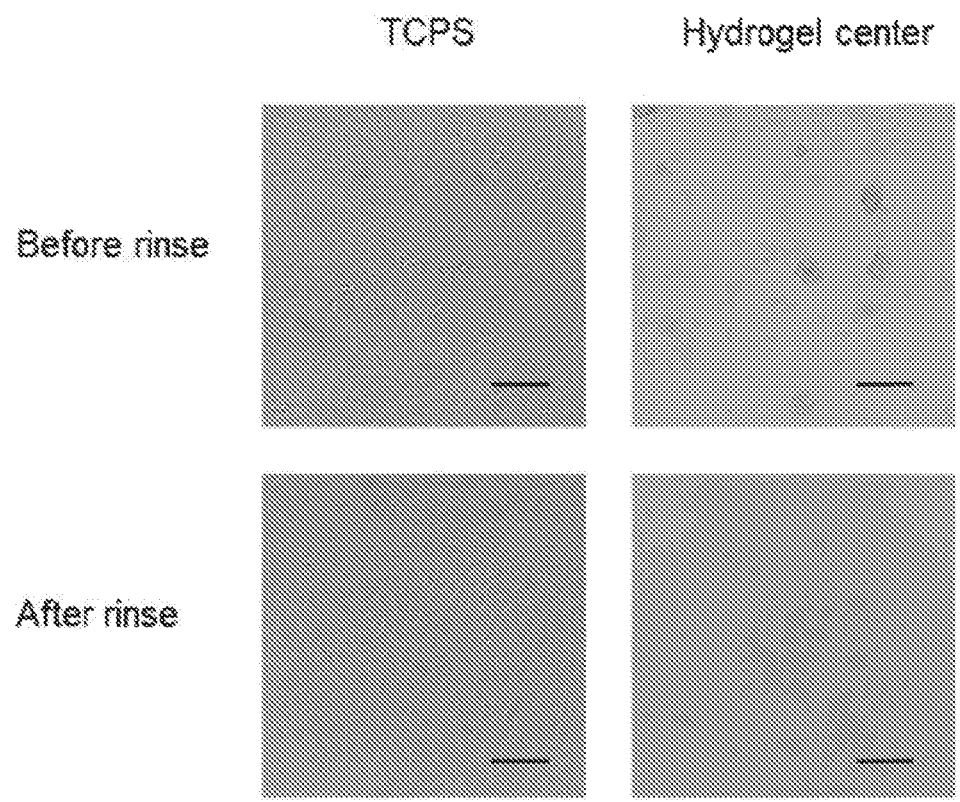
FIG. 12 compares phase-contrast images of NIH-3T3 cells adhered on TCPS and polyectoine hydrogel surfaces after 3 days of culturing. Cells adhered with a large quantity and spread by extending thin pseudopodia on the surfaces of TCPS before (a) and after rinsing (c). However, cells could not adhere to but aggregated on the poly(ectoine) hydrogel surface before rinsing (b) and were completely washed away after rinsing (d).

Moreover, the fibroblast NIH-3T3 cells, one of the most frequently used lines in materials/cell interaction research, was selected for the cell adhesion test of the polyectoine hydrogel. FIG. 12 compares both cell adhesion behaviors before and after rinse. Before rinse, NIH-3T3 cells cannot attach on the surface of polyectoine hydrogel (Hydrogel center), and instead tend to form cell aggregates. Conversely, NIH-3T3 cells can recognize and bind to the TCPS surface with a large quantity via non-specific adhesion, resulting in spreading with the extension of thin pseudopodia. After rinse, all the aggregated cells are washed away on the surface of polyectoine, but cells remain strongly bound on the TCPS surface. The nonfouling properties of polyectoine hydrogel are considered as the reason for the formation of cell aggregates on its surface. NIH-3T3 cells migrating on the surface of polyectoine hydrogel need to establish focal contacts with the neighboring matrix. However, NIH-3T3 cells cannot form stable bonds with polyectoine hydrogel, so they only establish cell contacts with polyectoine hydrogel to form cell aggregates.

While illustrative embodiments have been illustrated and described, it will be appreciated that various changes can be made therein without departing from the spirit and scope of the invention.

The embodiments of the invention in which an exclusive property or privilege is claimed are defined as follows:

1. A substrate surface coated with a layer of one or more N-oxide polymers or one or more N-oxide copolymers, wherein the N-oxide polymer or N-oxide copolymer has repeating units of formula (IV) or (V):

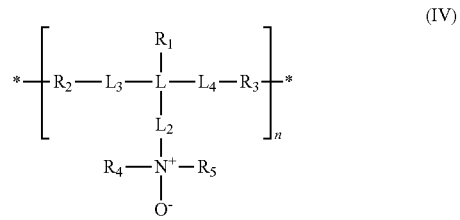

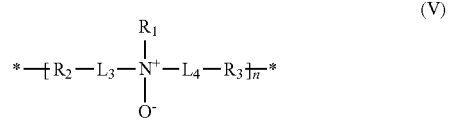

wherein indicates the point of attachment of the repeating unit to other repeating units in the polymer or copolymer;

$R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from functional groups suitable for polymerization by addition, condensation or free radical polymerization;

$R_4$ and $R_5$ are independently selected from the group consisting of hydrogen, $C_1$-$C_{20}$ alkyl, and $C_6$-$C_{12}$ aryl, cyclic alkyl;

L is C or Si;

$L_2$ is independently selected from —$(CH_2)_x$— or —$(CH(CN))_x$—, where x is an integer from 1 to 20; and $L_3$ and $L_4$ are independently selected from —$(CH_2)$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 1 to 20; and n is an integer from about 10 to about 500, wherein the substrate is a biomedical device selected from the group consisting of catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

2. A substrate surface coated with a layer of one or more N-oxide polymers or one or more N-oxide copolymers, wherein the N-oxide polymer or N-oxide copolymer has a repeating unit of formula (III):

(III)

wherein indicates the point of attachment of the repeating unit to other repeating units in the polymer or copolymer;

B is a polymer backbone;

L is selected from the group consisting of —$(CH_2)_x$—, —$(CH(CN))_x$—, —$C(=O)NH(CH_2)_x$—, —$C(=O)O(CH_2)_x$—, —$C(=O)OC(=O)O(CH_2)_x$—, —$(CH_2)_x$—O—$(CH_2)_x$—, and —$(CH_2)_x$—S—S—$(CH_2)_x$—, where x at each occurrence is an integer independently selected from 1 to 20;

$R_1$ and $R_2$ are independently selected from the group consisting of hydrogen, $C_1$-$C_{20}$ alkyl, and $C_6$-$C_{12}$ aryl, cyclic alkyl; and n is an integer from about 10 to about 500, wherein the substrate is a biomedical device selected from the group consisting of catheters, ear drainage tubes, feeding tubes, glaucoma drainage tubes, hydrocephalous shunts, keratoprosthesis, nerve guidance tubes, tissue adhesives, x-ray guides, artificial joints, artificial heart valves, artificial blood vessels, pacemakers, left ventricular assist devices (LVAD), artery grafts, vascular grafts, stents, intravascular stents, cardiac valves, joint replacements, blood vessel prostheses, skin repair devices, cochlear replacements, contact lenses, artificial ligaments and tendons, dental implants, and tissue scaffolds for regenerative tissue engineering.

3. The substrate surface of claim 1, wherein the surface has a fibrinogen adsorption less than about 200 ng/cm², less than about 100 ng/cm², less than about 50 ng/cm², less than about 20 ng/cm², or less than about 10 ng/cm².

4. The substrate surface of claim 1, wherein the surface has a fibrinogen adsorption less than about 5 ng/cm².

5. The substrate surface of claim 1, wherein N-oxide polymer or copolymer is a random, a multiblock, or star polymer or copolymer.

6. The substrate surface of claim 1, wherein N-oxide polymer or copolymer is prepared from a monomer having formula (I) or (II):

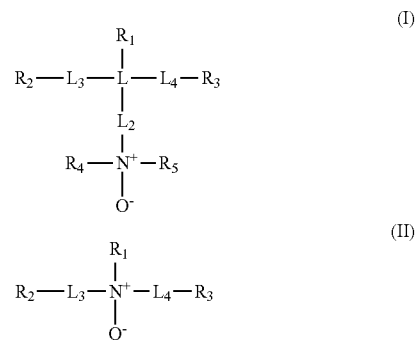

wherein $R_1$ is selected from the group consisting of hydrogen, fluorine, trifluoromethyl, cyano, $C_1$-$C_{20}$ alkyl, and $C_6$-$C_{12}$ aryl;

$R_2$ and $R_3$ are independently selected from functional groups suitable for polymerization by addition, condensation or free radical polymerization;

$R_4$ and $R_5$ are independently selected from the group consisting of hydrogen, $C_1$-$C_{20}$ alkyl, and $C_6$-$C_{12}$ aryl;

L is C or Si;

$L_2$ is independently selected from —$(CH_2)_x$— or —$(CH(CN))_x$—, where x is an integer from 1 to 20; and $L_3$ and $L_4$ are independently selected from —$(CH_2)$—, —$(CH(CN))_x$—, —$C(=O)NH(CH_2)_x$—, —$C(=O)O(CH_2)_x$—; —$C(=O)OC(=O)O(CH_2)_x$—; —$(CH_2)_x$—O—$(CH_2)_x$—, and —$(CH_2)_x$—S—S—$(CH_2)_x$—, where x at each occurrence is an integer independently selected from 1 to 20.

7. The substrate surface of claim 1, wherein N-oxide polymer or copolymer is prepared from a monomer selected from N-oxide acrylates, N-oxide acrylamides, N-oxide methacrylates, N-oxide methacrylamides, N-oxide vinyl compounds, N-oxide epoxides, and mixtures thereof.

8. The substrate surface of claim 2, wherein the polymer backbone is selected from the group consisting of a polyester, a polypeptide, a polyimide, a polyphosphazene, a polysiloxane, a polyepoxy, a vinyl polymer, a phenolic polymer, a polyurethane, a polyurea, a polycarbonate, a polysulfone, and a polysulfide.

9. The substrate surface of claim 2, wherein the surface has a fibrinogen adsorption less than about 200 ng/cm², less than about 100 ng/cm$^2$, less than about 50 ng/cm$^2$, less than about 20 ng/cm$^2$, or less than about 10 ng/cm$^2$.

10. The substrate surface of claim 2, wherein the surface has a fibrinogen adsorption less than about 5 ng/cm$^2$.

11. The substrate surface of claim 2, wherein N-oxide polymer or copolymer is a random, a multiblock, or star polymer or copolymer.

12. The substrate surface of claim 2, wherein N-oxide polymer or copolymer is prepared from a monomer selected from N-oxide acrylates, N-oxide acrylamides, N-oxide methacrylates, N-oxide methacrylamides, N-oxide vinyl compounds, N-oxide epoxides, and mixtures thereof.

* * * * *